United States Patent [19]

Honoreé et al.

[11] Patent Number: 5,061,706

[45] Date of Patent: Oct. 29, 1991

[54] 2,3-QUINOXALINEDIONES FOR USE AS NEUROLEPTICS

[75] Inventors: Tage Honoreé, Cøpenhagen; Poul Jacobsen, Rødovre; Flemming E. Nielsen, Virum; Lars Nafrim, Gentofte, all of Denmark

[73] Assignee: Novo Nordisk A/S, Bagsvaerd, Denmark

[21] Appl. No.: 452,029

[22] Filed: Dec. 15, 1989

[30] Foreign Application Priority Data

Dec. 22, 1988 [DK] Denmark .............................. 7158/88

[51] Int. Cl.$^5$ .................... A61K 31/495; C07D 241/44
[52] U.S. Cl. ...................................... 514/249; 544/354; 558/411; 558/417; 558/418; 560/13; 560/22; 560/43; 564/87; 564/442; 568/306
[58] Field of Search .......................... 514/249; 544/354

[56] References Cited

U.S. PATENT DOCUMENTS 3,992,378 11/1976 St. Clair et al. ..................... 544/354
4,812,458  3/1989 Honore et al. ...................... 544/354

OTHER PUBLICATIONS

Page et al. Chemical Abstracts, vol. 86, No. 114929 (1977) (Abstract for *Xenobiotica*, pp. 713–723 (1976.).
McFarlane et al., Chemical Abstracts, vol. 109, No. 110373 (1988) (Abstract for *Tet. Lett.* pp. 6363–6366 (1987).).
Page, J. G. et al. *Xenobiotica, 1976, vol. 6, No. 12, pp. 713–723*.
McFarlane, M. D. et al., *Tetrahedron Letters*, vol. 28, No. 50, pp. 6363–6366, 1987.

*Primary Examiner*—Hukund J. Shah
*Assistant Examiner*—E. Beinhardt
*Attorney, Agent, or Firm*—Steve T. Zelson; Elias J. Lambiris

[57] ABSTRACT

Heterocyclic dihydroxyquinoxaline compounds having the formula

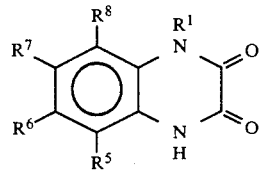

wherein
$R^1$ is hydroxy, alkoxy, aryloxy, aralkyloxy, cycloalkylalkoxy, cycloalkoxy, or acyloxy; and
$R^5$, $R^6$, $R^7$ and $R^8$ independently are hydrogen, $NO_2$, halogen CN, $SO_2NR'R'$, $SO_2R'$, $CF_3$, or $OR'$, wherein $R'$ is hydrogen or $C_{1-4}$-alkyl;

The invention also relates to a method of preparing the compounds, pharmaceutical compositions thereof, and their use.

The compounds are useful in the treatment of indications caused by hyperactivity of the excitatory neurotransmitters, particularly the quisqualate receptors, and especially as neuroleptics.

10 Claims, No Drawings

2,3-QUINOXALINEDIONES FOR USE AS NEUROLEPTICS

The present invention relates to therapeutically active heterocyclic compounds, a method of preparing the same, pharmaceutical compositions comprising the compounds, and a method of treating therewith.

L-glutamic acid, L-aspartic acid and a number of other closely related amino acids have in common the ability to activate neurons in the central nervous system (CNS). Biochemical, electrophysiological and pharmacological studies have substantiated this and demonstrated that acidic amino acids are transmitters for the vast majority of excitatory neurons in the mammalian CNS.

Interaction with glutamic acid mediated neurotransmission is considered a useful approach in the treatment of neurological and psychiatric diseases. Thus, known antagonists of excitatory amino acids have shown potent antiepileptic and muscle relaxant properties (A. Jones et al., Neurosci. Lett. 45, 157-61 (1984) and L. Turski et al., Neurosci. Lett. 53, 321-6 (1985)).

It has been suggested that accumulation of extracellular excitatory and neurotoxic amino acids, followed by hyperstimulation of neurons, may explain the neuronal degenerations seen in neurological diseases as Huntingtons chorea, Parkinsonism, epilepsia, senile dementia, and deficiencies of mental and motoric performance seen after conditions of brain ischemia, anoxia and hypoglycemia (E. G. McGeer et al., Nature, 263, 517-19 (1976) and R. Simon et al., Science, 226, 850-2 (1984).

Excitatory amino acids exert their actions via specific receptors located postsynaptically or presynaptically. Such receptors are at present conveniently subdivided into three groups based on electrophysiological and neurochemical evidence: 1 the NMDA (N-methyl-D-aspartate) receptors, 2 the quisqualate receptors, and 3 the kainate receptors. L-glutamic acid and L-aspartic acid probably activate all the above types of excitatory amino acid receptors and possibly other types as well.

The consequence of excitatory amino acid interaction with postsynaptic receptors is an increase in intracellular cGMP levels (G. A. Foster et al., Life Sci. 27, 215-21 (1980)) and an opening of $Na^+$-channels (A. Luini et al., Proc. Natl. Acad. Sci. 78, 3250-54 (1981)). $Na^+$-influx in the neurons will depolarize the neuronal membranes initiate an action potential and ultimately lead to a release of transmitter substance from the nerve terminal. The effects of test compounds on the above mentioned secondary responses to receptor interaction can be tested in simple in vitro systems.

The above mentioned classification of excitatory amino acid receptors into NMDA, quisqualate, and kainate receptors is based primarily on the following electrophysiological and neurochemical findings.

1) N-methyl-D-aspartate (NMDA) receptors exhibit high selectivity for the excitant NMDA. Ibotenic acid, L-homocysteic acid, D-glutamic acid and trans-2,3-piperidine dicarboxylic acid (trans-2,3-PDA) exert a strong to moderate agonist activity on these receptors. The most potent and selective antagonists are the D-isomers of the 2-amino-5-phosphonocarboxylic acids, e.g., 2-amino-5-phosphono-valeric acid (D-APV) and 2-amino-7-phosphonoheptanoic acid (D-APH), while moderate antagonist activity is shown by the D-isomers of long chain 2-amino dicarboxylic acids (e.g., D-2-amino-adipic acid) and long chain diaminodicarboxylic acids (e.g., diaminopimelic acid). The NMDA-induced synaptical responses have been extensively investigated in the mammalian CNS, especially in the spinal cord (J. Davies et al., J. Physiol. 297, 621-35 (1979) and the responses have been shown to be strongly inhibited by $Mg^{2+}$.

2) Quisqualate receptors are activated selectively by quisqualic acid, other potent agonists being AMPA (2-amino-3-hydroxy-5-methyl-4-isoxazolepropionic acid) and L-glutamic acid. Glutamic acid diethyl ester (GDEE) is a selective but very weak antagonist of this site. Quisqualate receptors are relatively insensitive to $Mg^{2+}$.

It is well known that an excitatory aminoacid projection from prefrontal cortex to nucleus accumbens (a special part of the forebrain having dopamine neurons) exists (Christie et al., J. Neurochem. 45, 477-82 (1985)). Further it is well known that glutamate modulates the dopaminergic transmission in the striatum (Rudolph et al. Neurochem.int. 5, 479-86 (1983)) as well as the hyperactivity connected with presynaptic stimulation of the dopamine system with AMPA in nucleus accumbens (Arnt. Life Sci. 28, 1597-1603 (1981)).

Quisqualate antagonists are therefore useful as a new type of neuroleptic.

3) Kainate receptors. Excitatory responses to kainic acid are relatively insensitive to antagonism by NMDA-antagonists and by GDEE, and it has been proposed that kainic acid activates a third subclass of acidic amino acid receptor. Certain lactonized derivatives of kainic acid are selective antagonists (O. Goldberg et al., Neurosci. Lett. 23, 187-91 (1981)) and the dipeptide 3-glutamyl-glycine also shows some selectivity for kainate receptors. $Ca^{2+}$) but not $Mg^{2+}$ is a strong inhibitor of kainic acid binding.

The affinity of a substance for one or more of the different types of excitatory amino acid receptors may be studied in simple binding experiments. In essense, the method involves incubation of a particular selected radiolabelled ligand and the particular specific substance to be investigated with brain homogenate which contains the receptor. Measurement of receptor occupancy is made by determination of the radioactivity bound to the homogenate and subtraction of nonspecific binding.

Quisqualate receptor binding may be studied by using $^3H$-AMPA as radioligand.

The influence of glutamic acid analogues on secondary effects of glutamate receptor interactions may be studied in vitro by using brain slices. Such experiments will provide information as to the efficacies (agonist/antagonist) of the test substances. This is in contrast to binding studies, which only provide information on the affinities of the compounds for the receptor.

It has now been found that the heterocyclic compounds of the invention have affinity for the quisqualate receptors and are antagonists in connection with this type of receptor which makes them useful in the treatment of any of the numerous indications caused by hyperactivity of excitatory amino acids and more specifically as neuroleptics.

Some compounds of the present invention have also shown glycine receptor activity.

The heterocyclic compounds of the invention have the general formula I

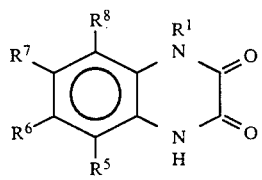

wherein $R^1$ is hydroxy, alkoxy, aryloxy, aralkyloxy, cycloalkylalkoxy, cycloalkoxy, or acyloxy; or $R^5$, $R^6$, $R^7$ and independently are hydrogen, $NO_2$, halogen, $CN$, $SO_2NR'R'$, $SO_2R'$, $CF_3$, or $OR'$, wherein $R'$ is hydrogen or $C_{1-4}$-alkyl;

The invention also relates to a method of preparing the above-mentioned compounds. This method comprises a) reducing a compound having the formula II

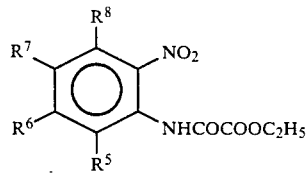

wherein $R^5$, $R^6$, $R^7$ and $R^8$ have the meanings set forth above, and optionally reacting the product thus formed with a compound having the formula III $$R^1-X \qquad III$$

wherein $R^1$ has the meaning set forth above, and X is a leaving group to form a compound of the formula I.

The pharmacological properties of the compounds of the present invention can be illustrated by determining their capability for displacing radioactively labelled 2-amino-3-hydroxy-5-methyl-4-isoxazolepropionic acid (AMPA) from the quisqualate type receptors. The antagonistic properties of the compounds is demonstrated by their capability to antagonize quisqualic acid stimulated $^3H$-GABA-efflux from cultured rat cortical neurones.

The displacement activity of the compounds may be shown by determining the $IC_{50}$ value which represents the concentration ($\mu g/ml$) which causes a displacement of 50% of the specific binding of $^3H$-AMPA.

The antagonism is measured by determining the $EC_{50}$ value which represents the concentration which reduces the rate of quisqualic acid stimulated $^3H$-GABA efflux by 50%.

$^3H$-AMPA binding

500 $\mu l$ of thawed rat cerebral cortical membrane homogenate in Tris-HCl (30 mM), $CaCl_2$ (2.5 mM) and KSCN (100 mM) pH 7.1 were incubated at 0° C. for 30 min. with 25 $\mu l$ $^3H$-AMPA (5 nM final concentration) and the test compound and buffer. Nonspecific binding was determined by incubation with L-glutamic acid (600 $\mu M$ final concentration). The binding reaction was terminated by adding 5 ml of ice-cold buffer followed by filtration through Whatman GF/C glass fibre filters and 2×5 ml wash with ice-cold buffer. Bound radioactivity was measured by scintillation counting. $IC_{50}$ was determined by Hill analysis of at least four concentrations of test compound.

CELL CULTURES

Cerebral cortices of 16 day old mouse embryos are chopped in 0.4×0.4 mm cubes. The tissue is dissociated by mild trypsinization (0.1% (wt/vol) trypsin, 37° C., 15 min) and subsequently inoculated into poly-L-lysine-coated 3 cm Petri dishes containing a slightly modified DMEM (24.5 mM KCl, 30 mM glucose) supplemented with p-aminobenzoate (7 $\mu M$), insulin (100 mU/1) and 10% (vol/vol) horse serum. Cells are maintained in culture for 5–7 days with the addition of the antimitotic agent cytosine arbinoside (40 $\mu M$) from day 2 in vitro to prevent glial proliferation. For further details and references see Drejer et al. (Exp. Brain Res. 47, 259 (1982)).

RELEASE EXPERIMENTS

Release experiments are performed using the model described by Drejer et al. (Life Sci. 38, 2077 (1986)). Cerebral cortex interneurons cultured in Petri dishes (30 mm) are added 100 $\mu M$ gamma-vinyl-GABA one hour before the experiment in order to inhibit degradation of GABA in the neurons. 30 min. before the experiment 5 $\mu Ci$ $^3H$-GABA is added to each culture and after this preloading period the cell monolayer at the bottom of the dish is covered with a piece of nylon mesh to protect the cells against mechanical damage and to facilitate dispersion of medium over the cell layer. The preloading medium is removed and the Petri dishes are placed in a superfusion system. This system consists of a peristaltic pump continuously delivering thermostated 37° C. superfusion medium (HEPES buffered saline (HBS): 10 mM HEPES, 135 mM NaCl, 5 mM KCl, 0.6 mM $MGSO_4$, 1.0 mM $CaCl_2$ and 6 mM D-glucose; pH 7.4) from a reservoir to the top of the slightly tilted Petri dish. The medium is continuously collected from the lower part of the dish and delivered to a fraction collector. Initially, the cells are superfused with HBS for 15 min. (flow rate 2 ml/min.). The cells are stimulated for 30 sec. every 4 min. by changing the superfusion medium from HBS to a corresponding medium containing quisqualate and test compound. The release of $^3H$-GABA in the presence of quisqualate (stimulated release in cpm) are corrected for the mean basal release (Cpm) before and after the stimulation.

Test results obtained by testing some compounds employed in the present invention will appear from the following table 1.

TABLE 1

| Compound of example | $IC_{50}$ $\mu g/ml$ | $K_i$ $\mu g/ml$ |
| --- | --- | --- |
| 6 d | 0.15 | 0.08 |
| 30 d | 0.37 | 0.12 |
| 33 d | 0.14 | 0.02 |
| 34 e | 0.09 | 0.27 |

The pharmaceutical preparations or compositions comprising the compounds of the invention may be administered to humans or animals by oral or parenteral route.

An effective amount of the active compound or a pharmaceutically-acceptable salt thereof may be determined in accordance with the usual factors, such as the nature and severity of the condition and the weight of the mammal requiring treatment.

Conventional excipients are such pharmaceutically-acceptable organic or inorganic carrier substances suitable for parenteral or enteral application which do not deleteriously react with the active compounds.

Examples of such carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose, and polyvinylpyrrolidone.

The pharmaceutical preparations can be sterilized and mixed, if desired, with auxiliary agents, such as lubricants, preservatives, stabilizers, wetting agents, emulsifiers, salt for influencing osmotic pressure, buffers and/or coloring substances and the like, which do not deleteriously react with the active compounds.

Injectable solutions or suspensions, preferably aqueous solutions with the active compound dissolved in polyhydroxylated castor oil, are particularly suitable for parenteral administration.

Ampoules are convenient unit dosage forms.

Tablets, dragees, or capsules containing talc and/or a carrier or binder or the like are particularly suitable for oral administration. The carrier preferably is lactose and/or corn starch and/or potato starch.

A syrup, elixir, or the like can be used in the cases where a sweetened vehicle can be employed or is desired.

Generally, the compounds of this invention are dispensed in unit dosage form comprising 50-200 mg of active ingredient in or together with a pharmaceutically-acceptable carrier per unit dosage.

The dosage of the compounds according to this invention is 1-500 mg/day, e.g., about 100 mg per dose, when administered to patients, e.g., humans, as a drug.

A typical tablet which may be prepared by conventional tabletting techniques contains:

| Core: | |
| --- | --- |
| Active compound (as free compound or salt thereof) | 100 mg |
| Colloidal silicon dioxide (Aerosil ®) | 1.5 mg |
| Cellulose, microcryst. (Avicel ®) | 70 mg |
| Modified cellulose gum (Ac-Di-Sol ®) | 7.5 mg |
| Magnesium stearate | 1 mg |
| Coating: | |
| HPMC | approx. 9 mg |
| *Mywacett ® 9-40 T | approx. 0.9 mg |

*Acylated monoglyceride used as plasticizer for film-coating

The free quinoxaline compounds of the present invention which form alkali metal or alkaline earth metal salts may be employed in such salt form. Such alkali metal or earth alkali metal salts are ordinarily formed by reacting the quinoxaline compound with an equivalent amount or excess of the selected alkali metal or earth alkali metal as the hydroxide, frequently and suitably by admixture in the presence of a neutral solvent, from which the salt may be precipitated or recovered in other conventional manner, e.g., by evaporation. Administration of a compound of the invention is often preferably in the form of a pharmaceutically-acceptable water-soluble alkali metal or earth alkali metal salt thereof, and orally, rectally, or parenterally in the form of a pharmaceutical composition wherein it is present together with a pharmaceutically-acceptable, liquid or solid carrier or diluent.

The compounds of the invention, together with a conventional adjuvant, carrier, or diluent, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical composition and unit dosage forms thereof may comprise conventional ingredients in conventional proportions, with or without additional active compounds or principles, and such unit dosage forms may contain any suitable effective neuroleptic, especially quisqualate antagonistic, amount of the active ingredient commensurate with the intended daily dosage range to be employed. Tablets containing fifty (50) milligrams of active ingredient or, more broadly, ten (10) to two hundred (200) milligrams, per tablet, are accordingly suitable representative unit dosage forms.

Due to their high degree of neuroleptic, particularly quisqualate antagonistic, activity and their low toxicity, together presenting a most favorable therapeutic index, the compounds of the invention may be administered to a subject, e.g., a living animal body, in need of such neuroleptic treatment, elimination, alleviation, or amelioration of an indication which is sensitive to a change in the quisqualate receptor condition, often preferably in the form of an alkali metal or earth alkali metal salt thereof, concurrently, simultaneously, or together with a pharmaceutically-acceptable carrier or diluent, especially and preferably in the form of a pharmaceutical composition thereof, whether by oral, rectal or parenteral (including subcutaneous) route, in an effective amount. Suitable dosage ranges are 50-200 milligrams daily, preferably 50-100 milligrams daily, and especially 70-100 milligrams daily, depending as usual upon the exact mode of administration, form in which administered, the indication toward which the administration is directed, the subject involved and the body weight of the subject involved, and the preference and experience of the physician or veterinarian in charge. Such method of treating may be described as the treatment of an indication caused by or related to hyperactivity of the excitatory neurotransmitters, and particularly the quisqualate receptors, in a subject in need thereof, which comprises the step of administering to the said subject a neurologically- or neuroleptically-effective amount of a quisqualate antagonistic quinoxaline compound of the invention.

The invention will now be described in further detail with reference to the following examples.

EXAMPLE 1 a. 1-Chloro-4-ethoxalylamino-3-nitrobenzene

To a solution of 1.0 g (5.8 mmol) 4-chloro-2-nitroaniline and 0.85 ml (6.2 mmol) dry triethylamine in 50 ml dry tetrahydrofuran was added a solution of 0.7 ml (6.27 mmol) ethyl oxalylchloride in 10 ml dry tetrahydrofuran. The mixture was stirred at 25° C. for 1 h, and then filtered. The filtrate was evaporated, and the residue was stirred with water to give 1.32 g (84%) of 1-chloro-4-ethoxalylamino-3-nitrobenzene. M.p. 156°-7° C.

b. 7-Chloro-1-hydroxyquinoxaline-2,3(1H,4H)-dione

A solution of 0.5 g (1.83 mmol) 1-chloro-4-ethoxyalylamino-3-nitrobenzene in 15 ml dimethylformamide was hydrogenated at atm. pressure by using 30 mg 5% Pd-C as a catalyst. The reaction mixture was filtered and evaporated in vacuo. The residue was recrystallized (dimethylformamide-water) to give 0.25 g (65%) of 7-chloro-1-hydroxyquinoxaline-2,3(1H,4H)-dione. M.P. decomp. $^1$H-NMR (DMSO-d$_6$): 12.2 (1H, broad s), 7,2 (3H, m). MS (m/e): 212 (M+, 50%).

EXAMPLE 2 a. 1-Chloro-3-ethoxalylamino-4-nitrobenzene

To a solution of 1.0 g (5.8 mmol) 5-chloro-2-nitroaniline and 0.85 ml (6.2 mml) dry triethylamine in 50 ml dry tetrahydrofuran was added a solution of 0.7 ml (6.27 mmol) ethyl oxalylchloride in 10 ml dry tetrahydrofuran. The mixture was stirred at 25° C. for 1 h, and then filtered. The filtrate was evaporated, and the residue was stirred with water to give 1.0 g (63%) of 1-chloro-3-ethoxalylamino-4-nitrobenzene. M.p. 99°–100° C.

b. 6-Chloro-1-hydroxyquinoxaline-2,3(1H,4H)-dione

A solution of 0.5 g (1.83 mmol) 1-chloro-3-ethoxalylamino-4-nitrobenzene in 15 ml dimethylformamide was hydrogenated at atm. pressure by using 0.5 g Ra-Ni as a catalyst. The residue was stirred with ethanol to give 0.13 g (30%) of 6-chloro-1-hydroxyquinoxaline-2,3(1H,4H)-dione. M.p. decomp. $^1$H-NMR (DMSO-d$_6$): 11.8 (1H, broad s), 7.17 (3H, m). MS (m/e): 212 (M$^{30}$, 60%).

EXAMPLE 3 a. 4-Ethoxalylaminobenzonitril

To a solution of 5.0 g (42.4 mmol) 4-aminobenzonitril and 8 ml (58.4 mmol) dry triethylamine in 100 ml dry tetrahydrofuran was added a solution of 7 ml (63.0 mmol) ethyl oxalylchloride in 25 ml dry tetrahydrofuran. Stirring was continued at 25° C. for 1 h, and then the mixture was evaporated in vacuo. The residue was stirred with water to give 8.9 g (85%) of 4-ethoxalylaminobenzonitril. M.p. 187.8° C.

b. 4-Ethoxalylamino-3-nitrobenzonitril

To a mixture of 1.0 g (4.0 mmol) 4-ethoxalylaminobenzonitril in 4 ml glacial acetic acid was added 4 ml acetic anhydride. At 0° C. a solution of 1 ml 100% nitric acid in 2 ml glacial acetic acid was added dropwise, and after 15 min. further 1 ml 100% nitric acid was added. Stirring was continued at 0° C. for 1 h. The reaction mixture was poured into 50 ml ice-water to give 0.95 g (81%) of 4-ethoxalylamino-3-nitrobenzonitril. M.p. 151.8° C.

c. 7-Cyano-1-hydroxyquinoxaline-2,3(1H,4H)-dione

A solution of 5.0 g (19.0 mmol) 4-ethoxalylamino-3-nitrobenzonitril in 200 ml ethanol and 200 ml ethylacetate was hydrogenated at atm. pressure by using 5 g Ra-Ni as a catalyst. The catalyst was filtered off and washed several times with dimethylformamide. The combined filtrates was evaporated in vacuo. The residue was stirred with ethanol to give 2.4 g (62%) of 7-cyano-1-hydroxyquinoxaline-2,,3(1H,4H)-dione. M.p. decomp. $^1$H-NMR (DMSO-d$_6$): 12.3 (2H, m), 7.77 (1H, s), 7.4 (2H, dd).

EXAMPLE 4 a. 5-Chloro-2-ethoxalylaminobenzotrifluoride

To a solution of 2.0 g (10.0 mmol) 2-amino-5-chlorobenzotrifluoride and 1.4 ml (10.0 mmol) dry triethylamine in 25 ml dry tetrahydrofuran was added a solution of 1.2 ml (11.0 mmol) ethyl oxalylchloride in 5 ml dry tetrahydrofuran. Stirring was continued at 25° C. for 3 h, and then the mixture was filtered and evaporated in vacuo. The residue was stirred with ethanol-water to give 2.4 g (82%) 5-chloro-2-ethoxalylaminobenzotrifluoride. M.p. 55–58° C.

b. 5-Chloro-2-ethoxalylamino-3-nitrobenzotrifluoride

To a solution of 2.4 g (8.1 mmol) 5-chloro-2-ethoxalylaminobenzotrifluoride in 13 ml 95–97% sulfuric acid a solution of 12 ml 100% nitric acid in 24 ml 95–97% sulfuric acid was added dropwise at 0°–5° C. Stirring was continued at 25° C. for 20 min. The reaction mixture was poured into 100 ml ice-water to give an oil. Extraction with dichloromethane gave 2.1 g (76%) of 5-chloro-2-ethoxalylamino-3-nitrobenzotrifluoride as crystals. M.p. 100°–101° C.

c. 7-Chloro-1-hydroxy-5-trifluoromethylquinoxaline-2,3(1H,4H)-dione

To a solution of 1.0 g (2.94 mmol) 5-chloro-2-ethoxalylamino-3-nitrobenzotrifluoride in 75 ml tetrahydrofuran was added 25 ml dimethylformamide and 1.0 ml 25% aqueous ammonia. The mixture was hydrogenated at atm. pressure by using 100 mg 5% Pt-C as a catalyst. When the hydrogen uptake was completed, the catalyst was filtered off, and the filtrate was evaporated in vacuo. The residue was stirred with 1N aqueous hydrochloric acid to give 0.66 g (80%) of 7-chloro-1-hydroxy-5-trifluoromethylquinoxaline -2,3(1H,4H)-dione. M.P. 275° C. decomp. $^1$H-NMR (DMSO-d$_6$): 11.7 (2H, m), 7.60 (1H, d), 7.43 (1H, d).

EXAMPLE 5 a. 4,5-Dichloro-2-ethoxalylamino-1-nitrobenzen

To a solution of 1.0 g (4.8 mmol) 4,5-dichloro-2-nitroanilin and 1.0 ml (7.3 mmol) dry triethylamine in 100 ml dry tetrahydrofuran was added a solution of 0.9 ml (8.1 mmol) ethyloxalylchloride in 25 ml dry tetrahydrofuran. Stirring was continued at 25° C. for 3 h, and then the mixture was filtered and evaporated in vacuo. The residue was stirred with a mixture of ethanol and light petroleum to give 1.17 g (79%) of 4,5-dichloro-2-ethoxalylamino-1-nitrobenzen. M.p. 96°–97° C.

b. 6,7-Dichloro-1-hydroxyquinoxaline-2,3(1H,4H)-dione

To a solution of 0.4 g (1.3 mmol) 4,5-dichloro-2-ethoxalylamino-1-nitrobenzene in 30 ml tetrahydrofuran was added 10 ml dimethylformamide and 0.4 ml 25% aqueous ammonia. The mixture was hydrogenated at atm. pressure by using 50 mg 5% Pd-C as a catalyst. The precipitate was filtered off and washed with tetrahydrofuran. The filter cake was washed several times with 5% aqueous potassium hydroxide. Acidification of the filtrate with 4N hydrochloric acid gave 0.14 g (45%) of 6,7-dichloro-1-hydroxyquinoxaline-2,3(1H,4H)-dione. M.p. decomp. $^1$H-NMR (DMSO-d$_6$): 12.2 (2H, m), 7.50 (1H, s), 7.27 (1H, s). MS (m/e): 246 (M+, 35%).

EXAMPLE 6 a. 2-Cyano-5-nitrobenzotrifluoride

A solution of 10.0 g (48.5 mmol) 2-amino-5-nitrobenzotrifluoride in 60 ml glacial acetic acid was added 200 ml 2N hydrochloric acid, and then at 0° C. diazotized with a solution of 3.36 g (48.6 mmol) sodium nitrite in 100 ml water. Stirring was continued at 0° C. for 1 h, and then at 25° C. a solution of 18 g (75 mmol) potassium tetracyanonickelate (K$_2$NiCN$_4$) in 500 ml saturated sodium hydrogencarbonate was added dropwise. Extraction with ethyl acetate followed by distillation (95°-100° C./0.5 mmHg) of the crude oil gave 6.8 g (65%) of 2-cyano-5-nitrobenzotrifluoride.

b. 2-Cyano-5-ethoxalylaminobenzotrifluoride

A solution of 6.8 g (31.5 mmol) 2-cyano-5-nitrobenzotrifluoride in 200 ml ethanol was hydrogenated at atm. pressure by using 0.4 g 5% Pd-C as a catalyst. The reaction mixture was filtered and evaporated in vacuo. The crude product was dissolved in 150 ml dry tetrahydrofuran and added 6.0 ml (43.6 mmol) dry triethylamine. A solution of 4.4 ml (39.4 mmol) ethyl oxalylchlorid in 30 ml dry tetrahydrofuran was added dropwise, and then stirring was continued at 25° C. for 3 h. The filtered and evaporated reaction product was stirred with ethanol-water to give 7.3 g (82%) of 2-cyano-5-ethoxalylaminobenzotrifluoride. M.p. 112-114° C.

c. 2-Cyano-5-ethoxalylamino-4-nitrobenzotrifluoride

To 75 ml ice-cooled 100% nitric acid was added gradually 7.25 g (25.3 mmol) 2-cyano-5-ethoxalylaminobenzotrifluoride. Stirring was continued at 25° C. for 3 h. The reaction mixture was poured into 500 ml ice-water to give a crude product. Recrystallization (ethanol-water) gave 5.1 g (61%) 2-cyano-5-ethoxalylamino-4-nitrobenzotrifluoride. M.p. 101°-102° C.

d. 7-Cyano-1-hydroxy-6-trifluoromethylquinoxaline-2,3(1H,4H)-dione

To a solution of 10.5 g (31.7 mmol) 2-cyano-5-ethoxalylamino-4-nitrobenzotrifluoride in 450 ml ethanol was added 45 ml glacial acetic acid. The mixture was hydrogenated at atm. pressure by using 0.2 g 5% Pd-C as a catalyst. The filtered and evaporated reaction product was recrystallized (ethylacetate-light petroleum) to give 6.91 g (81%) of 7-cyano-1-hydroxy-6-trifluoromethyl-quinoxaline-2,3(1H,4H)-dione. M.p. 180° C. decomp. $^1$H-NMR (DMSO-d$_6$): 7.93 (1H, s), 7.53 (1H, s). MS (m/e): 271 (M+, 70%).

EXAMPLE 7 a. 5-Amino-2-chlorobenzonitrile

A solution of 10.0 g (54.8 mmol) 2-chloro-5-nitrobenzonitrile in 500 ml ethanol was hydrogenated at 30 psi by using 0.5 g 5% Pd-C as a catalyst When the hydrogen uptake had ceased, the reaction mixture was filtered and evaporated in vacuo. The residue was recrystallized (ethanol-water) to give 3.6 g (44%) of 5-amino-2-chlorobenzonitrile. M.p. 129°-130° C.

b. 2-Chloro-5-ethoxalylaminobenzonitrile

To a solution of 3.6 g (23.4 mmol) 5-amino-2-chlorobenzonitrile and 3.6 ml (26.2 mmol) dry triethylamine in 200 ml dry tetrahydrofuran was added a solution of 3.0 ml (26.9 mmol) ethyl oxalylchloride in 20 ml dry tetrahydrofuran. Stirring was continued at 25° C. for 2 h, and then the reaction mixture was filtered and evaporated in vacuo. The residue was stirred with water to give 5.8 g (99%) of 2-chloro-5-ethoxalylaminobenzonitrile. M.p. 182°-83° C.

c. 6-Chloro-3-ethoxalylamino-2-nitrobenzonitrile and 2-chloro-5-ethoxalylamino-4-nitrobenzonitrile To 75 ml ice-cooled 100% nitric acid was added gradually 8.1 g (32.1 mmol) 2-chloro-5-ethoxalylaminobenzonitrile. Stirring was continued at 0° C. for 1.5 h, and then the reaction mixture was poured into 500 ml ice-water. The precipitated product was filtered off and recrystallized (ethanol-water) to give 8.25 g (86%) of 6-chloro-3-ethoxalylamino-4-nitrobenzonitrile. M.p. 143-45° C. 1H-NMR (CDCl$_3$-DMSO-d$_6$): 11.3 (1H, broad s), 8.1 (2H, dd, J=10 Hz), 4.3 (2H, q), 1.4 (3H, t). The filtrate was extracted with 150 ml ethylacetate to give 2-chloro-3-ethoxalylamino-4-nitrobenzonitrile as an oil (0.67 g, 7%). $^1$H-NMR (CDCl$_3$-DMSO-d$_6$) 11.4 (1H, broad s), 8.57 (1H, s), 8.33 (1H, s), 4.3 (2H, q), 1.4 (3H, t).

d. 7-Chloro-8-cyano-1-hydroxyquinoxaline-2,3(1H,4H)-dione

To a solution of 1.0 g (3.36 mmol) 6-chloro-3-ethoxalylamino-2-nitrobenzonitrile in 75 ml tetrahydrofuran was added 25 ml dimethylformamide and 1.0 ml 25% aqueous ammonia. The mixture was hydrogenated at atm. pressure by using 100 mg 5% Pd-C as a catalyst. The precipitated product was filtered off and washed with tetrahydrofuran. The filter cake was washed several times with 5% aqueous potassium hydroxide. Acidification of the filtrate with 4N hydrochloric acid gave 0.57 g (72%) of 7-chloro-8-cyano-1-hydroxyquinoxaline-2,3(1H,4H)-dione. M.p. 280° C. decomp H-NMR (DMSO-d$_6$) 12.3 (2H, broad s), 7.5 (2H, s). MS (m/e): 237 (M+, 10%).

EXAMPLE 8 a. 4-Ethoxalylaminophthalamide

To a solution of 13.9 g (77.5 mmol) 4-aminophthalamide in 250 ml dry dimethylformamide was added 12.0 ml (86.4 mmol) dry triethylamine and then dropwise a solution of 10.1 ml (88.7 mmol) ethyl oxalylchloride in 50 ml dry dimethylformamide. Stirring was continued at 25° C. for 1 h. The reaction mixture was poured into 800 ml ice-cooled methanol to give 15.8 g (73%) of 4-ethoxalylaminophthalamide. M.p. 229°-230° C.

b. 4-Ethoxalylaminophthalonitrile

To a suspension of 7.0 g (25.1 mmol) 4-ethoxalylaminophthalamide in 75 ml dry pyridine was gradually added 4.1 ml (44.8 mmol) phosphorus oxychloride. Stirring was continued at 25° C. for 30 min. The reaction mixture was poured into 300 ml ice-cooled 4N hydrochloric acid to give 4.7 g (77%) of 4-ethoxalylaminopthalonitrile. M.p. 193.7° C.

c. 4-Ethoxalylamino-5-nitrophthalonitrile and 4-Ethoxalylamino-3-nitrophthalonitrile To 50 ml ice-cooled 100% nitric acid was added gradually 2.0 g (8.2 mmol) 4-ethoxalylaminophthalonitrile. Stirring was continued at 25° C. for 48 h. The reaction mixture was poured into 300 ml ice-water to give 1.6 g crude product. Column chromatography (200 g kiselgel; eluents: toluene containing ethyl acetate) gave 0.7 g (30%) 4-ethoxalylamino-5-nitrophthalonitrile. M.p. 140°-141° C. $^1$H-NMR (DMSO-d$_6$): 11.7 (1H, s), 8.97 (1H, s), 8.70 (1H, s), 4.4 (2H, q), 1.4 ($^3$H, t), and 0.75 g (32%) 4-ethoxalylamino-3-nitrophthalonitrile. M.p. 140–141° C. 1H-NMR (DMSO-d$_6$) 11.7 (1H, s), 8.4 (2H, dd, J=9Hz), 4,4 (2H, q), 1.4 (3H, t).

d.
6,7-Dicyano-1-hydroxyquinoxaline-2,3(1H,4H)-dione

A solution of 0.8 g (3.03 mmol) 4-ethoxalylamino-5-nitrophthalonitrile in 50 ml dimethylformamide was hydrogenated at atm. pressure by using 25 mg 5% Pd-C as a catalyst. When the hydrogen uptake had ceased, the reaction mixture was filtered and evaporated in vacuo. The residue was recrystallized (dimethylformamide-water) to give 0.4 g (66%) of 6,7-dicyano-1-hydroxyquinoxaline-2,3(1H,4H)-dione. M.p. decomp. $^1$H-NMR (DMSO-d$_6$): 7.97 (1H, s), 7.57 (1H, s). MS (m/e): 228 (M$^+$, 80%).

EXAMPLE 9

7-Cyano-1-phenoxycarbonyloxy-6-trifluoromethyl-quinoxaline-2,3(1H,4H)-dione

A solution of 0.4 g (1.48 mmol) 7-cyano-1-hydroxy-6-trifluoromethylquinoxaline -2,3(1H,4H)-dione in 50 ml dry tetrahydrofuran was added 0.225 ml (1.63 mmol) dry triethylamine and 0.2 ml (1.58 mmol) phenyl chloroformate. The mixture was stirred at 25° C. for 30 min., and then filtered and evaporated in vacuo. The residue was stirred with ether to give 0.48 g (83%) of 7-cyano-1-phenoxycarbonyloxy-6-trifluoromethylquinoxaline-2,3-(1H,4H)-dione. M.p. 190° C. decomp. $^1$H-NMR (DMSO-d$_6$): 8.43 (1H,s), 7.63 (1H, s), 7.3 (5H, broad s).

EXAMPLE 10

7-Cyano-1-propionyloxy-6-trifluoromethyl-quinoxaline-2,3(1H,4H)-dione

A solution of 0.4 g (1.48 mmol) 7-cyano-1-hydroxy-6-trifluoromethylquinoxaline -2,3(1H,4H)-dione in 50 ml dry tetrahydrofuran was added 0.25 ml (1.82 mmol) dry triethylamine and 0.15 ml (1.72 mmol) propionyl chloride. The mixture was refluxed for 30 min., and then evaporated in vacuo. The residue was stirred with water to give 0.46 g (95%) 7-cyano-1-propionyloxy-6-trifluoromethyl-quinoxaline-2,3(1H,4H)-dione. M.p. 227° C. $^1$H-NMR (DMSO-d$_6$): 8.37 (1H, s), 7.73 (1H, s), 4.5 (2H, q), 1.35 (3H, t).

EXAMPLE 11

7-Cyano-1-ethoxycarbonyloxy-6-trifluoromethyl-quinoxaline-2,3(1H,4H)-dione

A solution of 0.4 g (1.48 mmol) 7-cyano-1-hydroxy-6-trifluoromethylquinoxaline-2,3(1H,4H)-dione in 50 ml dry tetrahydrofuran was added 0.2 ml (1.50 mmol) dry triethylamine and 0.15 ml (1.58 mmol) ethylchloroformate. The mixture was refluxed for 45 min., and then evaporated in vacuo. The residue was stirred with water to give 0.46 g (91%) of 7-cyano-1-ethoxycarbonyloxy-6-trifluoromethylquinoxaline-2,3(1H,4H)-dione. M.p. 190° C. decomp. $^1$H-NMR (DMSO-d$_6$): 8.33 (1H, s), 7.73 (1H, s), 2.9 (2H, q), 1.2 (3H, t).

EXAMPLE 12

1-Benzoyloxy-7-cyano-6-trifluoromethylquinoxaline-2,3(1H,4H)-dione

A solution of 0.4 g (1.48 mmol) 7-cyano-1-hydroxy-6-trifluoromethylquinoxaline-2,3(1H,4H)-dione in 50 ml dry tetrahydrofuran was added 0.2 ml (1.45 mmol) dry triethylamine and 0.175 ml (1.50 mmol) benzoyl chloride. The mixture was refluxed for 30 min., and then evaporated in vacuo. The residue was stirred with water to give 0.54 g (98%) of 1-benzoyloxy-7-cyano-6-trifluoromethylquinoxaline-2,3(1H,4H)-dione. M.p. 186° C. $^1$H-NMR (DMSO-d$_6$): 8.47 (1H, s), 8.2 (2H, m), 7.8 (4H, m).

EXAMPLE 13

1-Acetoxy-7-cyano-6-trifluoromethylquinoxaline-2,3(1H,4H)-dione

A solution of 0.4 g (1.48 mmol) 7-cyano-1-hydroxy-6-trifluoromethylquinoxaline-2,3(1H,4H)-dione in 50 ml dry tetrahydrofuran was added 0.3 ml (2.18 mmol) dry triethylamine and 0.15 ml (2.10 mmol) acetyl chloride. The mixture was refluxed for 3 h, and then evaporated in vacuo. The residue was stirred with water to give 0.42 g (92%) of 1-acetoxy-7-cyano-6-trifluoromethyl-quinoxaline-2,3(1H,4H)-dione. M.p. 230° C. $^1$H-NMR (DMSO-d$_6$): 8.16 (1H, s), 7.53 (1H, s), 2.37 (3H, s).

EXAMPLE 14 a. N-Ethoxalyl-3,5-bistrifluoromethylaniline

To a solution of 3.0 ml (19.2 mmol) 3,5-bistrifluoromethylaniline in 100 ml dry tetrahydrofuran was added 3.0 ml (21.4 mmol) dry triethylamine. The reaction mixture was cooled to 0° C. and 2.3 ml (20.6 mmol) ethyl oxalylchloride in 25 ml dry tetrahydrofuran was added dropwise. Stirring was continued at 25° C. for 1 h. The reaction mixture was filtered and evaporated in vacuo. The residue was stirred with n-pentane, and the precipitate was filtered off to give 4.8 g (76%) of N-ethoxalyl-3,5-bistrifluoromethylaniline. M.p. 86.8° C.

b. N-Ethoxalyl-3,5-bistrifluoromethyl-2-nitroaniline

To a solution of 4.3 g (13 mmol) N-ethoxalyl-3,5-bistrifluoromethylaniline in 15 ml concentrated sulfuric acid was added at 0° C. 1.5 g (15 mmol) potassium nitrate. Stirring was continued at 0° C. for 90 min., and then at 25° C. for 120 min. The reaction mixture was poured into 100 ml ice-water and the precipitate was filtered off. The crude product was purified by column chromatography on silica gel with toluene/ethylacetate 5:1 as eluent, to give 0.44 g (9%) of N-ethoxalyl-3,5-bistrifluoromethyl-2-nitroaniline. M.p. 115.0° C.

c.
6,8-Bistrifluoromethyl-1-hydroxyquinoxaline-2,3(1H,4H)dione 0.20 g (0.5 mmol) N-ethoxalyl-3,5-bistrifluoromethyl-2-nitroaniline in 10 ml tetrahydrofuran:dimethylformamide:25% aqueous ammonia (30:10:0.7) was hydrogenated at atm. pressure by using 5% Pd-C (0.02 g) as a catalyst. The reaction mixture was filtered and evaporated in vacuo. The residue was stirred with water, and the precipitate was filtered off to give 0.11 g (84%) of 6,8-bistrifluoromethyl-1-hydroxyquinoxaline-2,3(1H,4H)-dione. M.p. decomp. $^1$H-NMR (DMSO-d$_6$): 8.1 (s). MS (m/e): 314 (M$^+$, 40%), 173 (45%), 69 (100%).

EXAMPLE 15 a. N-Ethoxalyl-4-methoxy-2-nitroaniline

To a solution of 3.0 g (18 mmol) 4-methoxy-2-nitroaniline in 100 ml dry tetrahydrofuran was added 6 ml (43 mmol) dry triethylamine. The reaction mixture was cooled to 0° C. and 3.4 ml (30 mmol) ethyl oxalylchloride in 50 ml dry tetrahydrofuran was added dropwise. Stirring was continued at 25° C. for 1 h. The reaction mixture was filtered and evaporated in vacuo. The residue was stirred with ether, and the precipitate was filtered off to give 1.4 g (29%) of N-ethoxalyl-4-methoxy-2-nitroaniline. M.p. 151.3° C.

b. 1-Hydroxy-7-methoxyquinoxaline-2,3(1H,4H)-dione 0.10 g (0.4 mmol) N-ethoxalyl-4-methoxy-2-nitroaniline in 10 ml dimethylformamide was hydrogenated at atm. pressure by using 5% Pt-C (0.01 g) as a catalyst. The reaction mixture was filtered and 10 ml 1N hydrochloric acid was added. The reaction mixture was cooled to 0° C. and the precipitate was filtered off, washed with water, ethanol and ether to give 0.03 g (39%) of 1-hydroxy-7-methoxyquinoxaline-2,3(1H,4H)-dione. M.p. decomp. $^1$H-NMR (DMSO-d$_6$): 12.0 (broad s), 7.0 ($^3$H, m), 3.8 (3H, s). MS (m/e): 208 (M+, 70%), 163 (100%).

EXAMPLE 16 a. N-Ethoxalyl-4 5-dimethoxy-2-nitroaniline

To a solution of 1.0 g (5.1 mmol) 4,5-dimethoxy-2-nitroaniline and 2.0 ml (14.3 mmol) dry triethylamine in 50 ml dry tetrahydrofuran was added a solution of 1.1 ml (9.8 mmol) ethyl oxalylchloride in 25 ml dry tetrahydrofuran. The reaction mixture was stirred at 25° C. for 1 h, and then filtered. The filtrate was evaporated in vacuo and the residue was washed with ether and water to give 1.05 g (70%) of N-ethoxalyl-4,5-dimethoxy-2-nitroaniline. M.p. 162.7° C.

b. 1-Hydroxy-6,7-dimethoxyquinoxaline-2,3(1H,4H)-dione 0.15 g (0.5 mmol) N-ethoxyalyl-4,5-dimethoxy-2-nitroaniline in 10 ml dimethylformamide was hydrogenated at atm. pressure and 15° C. by using 5% Pt-C (15 mg) as a catalyst. The reaction mixture was filtered and evaporated in vacuo. The residue was washed with ether, ethanol and methanol to give 0.05 g (42%) of 1-hydroxy-6,7-dimethoxyquinoxaline-2,3(1H,4H)-dione. M.p. decomp. $^1$H-NMR (DMSO-d$_6$): 12.0 (1H, broad s), 7.3 (1H, s), 7.0 (1H, s), 3.9 (3H, s), 3.85 (3H, s). MS (m/e): 238 (M+, 60%), 193 (100%).

EXAMPLE 17

1-Hydroxy-5-methylquinoxaline-2,3(1H,4H)-dione

To a solution of 2.0 g (13.2 mmol) 6-methyl-2-nitroaniline and 4.0 ml (28,5 mmol) dry triethylamine in 50 ml dry tetrahydrofuran was added a solution of 2.0 ml (17.9 mmol) ethyl oxalylchloride in 20 l dry tetrahydrofuran. The reaction mixture was stirred at 80° C. for 15 min. After cooling to 25° C. the mixture was filtered and the filtrate was evaporated in vacuo to give an oil (2.0 g). 1.0 g of the oil in 25 ml tetrahydrofuran:dimethylformamide:25% aqueous ammonia (30:10:0.7) was hydrogenated at atm. pressure by using 100 mg 5% Pt-C as a catalyst. The precipitate was filtered off, and the filter cake was washed several times with 1N aqueous potassium hydroxide. Acidification of the filtrate with concentrated hydrochloric acid gave 0.08 g (6%) of 1-hydroxy-5-methylquinoxaline-2,3,(1H, 4H)-dione. M.p. decomp. (299° C.). $^1$H-NMR (DMSO-d$_6$): 11.5 (1H, broad s), 7.6–7.0 ($^3$H, m), 2.4 (3H, s).

EXAMPLE 18

7,8-Dicyano-1-hydroxyquinoxaline-2,3(1H,4H)-dione 2 g (0.9 mmol) 4-ethoxalylamino-3-nitrophthalonitrile in 15 ml tetrahydrofuran:dimethylformamide: 25% aqueous ammonia (30:10:0.7) was hydrogenated at atm. pressure by using 25 mg 5% Pt-C as a catalyst. The precipitate was filtered off and washed with tetrahydrofuran. The filter cake was washed several times with 1N aqueous potassium hydroxide. The filtrate was acidified with concentrated hydrochloric acid. The precipitate was filtered off and washed with water, ethanol and ether to give 0.120 g (76%) of 7,8-dicyano-1-hydroxyquinoxaline-2,3(1H,4H)-dione. M.p. decomp. $^1$H-NMR (DMSO-d$_6$): 7.7 (2H, dd). IR (KBr): 2240 (m). MS (m/e): 228 (M+, 3%), 184 (100%).

EXAMPLE 19 a. N-Ethoxalyl-5-methoxy-2-nitroaniline

To a solution of 0.6 g (3.6 mmol) 5-methoxy-2-nitroaniline and 1.0 ml (7.1 mmol) dry triethylamine in 25 ml dry tetrahydrofuran was added a solution of 0.8 ml (7.2 mmol) ethyl oxalylchloride in 10 ml dry tetrahydrofuran. The reaction mixture was stirred at 25° C. for 1 h, and then filtered. The filtrate was evaporated in vacuo and the residue was washed with cold ether and water to give 0.22 g (23%) N-ethoxalyl-5-methoxy-2-nitroaniline. M.p. 158.0° C.

b. 1-Hydroxy-6-methoxyquinoxaline-2,3(1H,4H)-dione 0.21 g (0.8 mmol) N-ethoxalyl-5-methoxy-2-nitroaniline in 10 ml dimethylformamide was hydrogenated at atm. pressure by using 10 mg 5% Pt-C as a catalyst. The reaction mixture was filtered and 5 drops of 25% aqueous ammonia was added to the filtrate. The precipitate was filtered off, and the filter cake was washed several times with 1N aqueous potassium hydroxide. The filtrate was acidified with concentrated hydrochloric acid, and the precipitate was filtered off, washed with water, ethanol and ether to give 0.07 g (44%) of 1-hydroxy-6-methoxyquinoxaline-2,3(1H,4H)-dione. M.p. decomp. $^1$H-NMR (DMSO-d ) 12.1 (1H, broad s), 7.6–6.6 (3H, m), 3.8 (3H, s). MS (m/e): 208 (M+, 50%), 163 (100%).

EXAMPLE 20 a. N-ethoxalyl-4,5-dimethyl-2-nitroaniline

To a solution of 5.0 g (30 mmol) 4,5-dimethyl-2-nitroaniline and 9.0 ml (64 mmol) dry triethylamine in 100 ml dry tetrahydrofuran was added a solution of 5.0 ml (45 mmol) ethyl oxalylchloride in 25 ml dry tetrahydrofuran. The reaction mixture was stirred at 80° C. for 30 min. After cooling to 25° C. the mixture was filtered and the filtrate was evaporated in vacuo. The residue was washed with ether to give 2.3 g (29%) of N-ethoxalyl-4,5-dimethyl-2-nitroaniline. M.p. 108.8° C.

b. 6,7-Dimethyl-1-hydroxyquinoxaline-2,3(1H,4H)-dione 1.0 g (3.8 mmol) 4,5-dimethyl-2-nitroaniline in 30 ml tetrahydrofuran:dimethylformamide: 25% aqueous ammonia (30:10:0.7) was hydrogenated at atm. pressure by using 60 mg 5% Pt-C as a catalyst. The precipitate was filtered off and washed with tetrahydrofuran. The filter cake was washed several times with 1N aqueous potassium hydroxide, and the filtrate was acidified with concentrated hydrochloric acid. The precipitate was filtered off and washed with water, ethanol and ether to give 0.13 g (17%) of 6,7-dimethyl-1-hydroxyquinoxaline-2,3(1H,4H)-dione. M.p. decomp. $^1$H-NMR (DMSO-d$_6$): 11.9 (1H, broad s), 7.3 (1H, s), 7.0 (1H, s), 2.3 (6H, s). MS (m/e): 206 (M+, 70%), 161 (100%).

EXAMPLE 21 a. N-Ethoxalyl-5-methyl-2-nitroaniline

N-ethoxalyl-5-methyl-2-nitroaniline was prepared in exactly the same manner as N-ethoxalyl-4,5-dimethyl-2-nitroaniline. Yield: 3.0 g (36%). M.p. 114.4° C.

b. 1-Hydroxy-6-methylquinoxaline-2,3(1H,4H)-dione 1-hydroxy-6-methylquinoxaline-2,3(1H,4H)-dione was prepared in exactly the same manner as 6,7-dimethyl-1-hydroxyquinoxaline-2,3(1H,4H)-dione. Yield: 0.22 g (29%). M.p. decomp. $^1$H-NMR (DMSO-d$_6$): 11.9 (1H, broad s), 7.5-6.7 (3H, m), 2.3 (3H, s). MS (m/e): 192 (M+, 65%), 147 (100%), 134 (45%).

EXAMPLE 22 a. N-Ethoxalyl-4-methyl-2-nitroaniline

N-ethoxalyl-4-methyl-2-nitroaniline was prepared in exactly the same manner as N-ethoxalyl-4,5-dimethyl-2-nitroaniline. Yield: 1.5 g (18%). M.p. 126.4° C.

b. 1-Hydroxy-7-methylquinoxaline-2,3(1H,4H)-dione 1-hydroxy-7-methylquinoxaline-2,3(1H,4H)-dione was prepared in exactly the same manner as 6,7-dimethyl-1-hydroxyquinoxaline-2,3(1H,4H)-dione. Yield: 0.15 g (20%). M.p. decomp. $^1$H-NMR (DMSO-d$_6$): 12.0 (1H, broad s), 7.4-6.8 (3H, m), 2.4 (3H, s). MS (m/e): 192 (M+, 80%), 147 (100%), 120 (75%).

EXAMPLE 23 a. 3-Ethoxalylamino-4-nitrobenzotrifluoride

A solution of ethyl oxalylchloride (0.47 ml, 4.2 mmol) in 10 ml of dry tetrahydrofuran was added dropwise to a solution of 3-amino-4-nitrobenzotrifluoride (0.82 g, 4.0 mmol) in 50 ml of dry tetrahydrofuran with stirring at room temperature. A solution of dry triethylamine (0.59 ml, 4.2 mmol) in 10 ml of dry tetrahydrofuran was added dropwise. Then the mixture was refluxed for 10 min.. and after cooling in an ice bath the triethylamine hydrochloride was filtered off. The filtrate was evaporated to dryness, and the residue was triturated with a mixture of ether and light petroleum to give 1.05 g (75%) of the title compound. M.p. 82°-83° C.; $^1$H-NMR (CDCl$_3$+DMSO-d$_6$): 1.45 (t, J=7 Hz, 3H, CH$_3$), 4.43 (q, J=7 Hz, 2H, CH$_2$), 7.55 (dd, J$_{6-7}$=9 Hz, J$_{6-2}$=2 Hz, 1H, H-6), 8.37 (d, J=9 Hz, 1H, H-5), 8.93 (d, J=2 Hz, 1H, H-2), 11.7 (broad s, 1H, NH).

b. 1-Hydroxy-6-trifluoromethylquinoxaline-2,3(1H,4H)-dione

A solution of 3-ethoxalylamino-4-nitrobenzotrifluoride (0.61 g, 2 mmol) in 50 ml of 96% ethanol was hydrogenated at atmospheric pressure and room temperature in the presence of 30 mg of 5% platinum on carbon for 5 min. The catalyst was filtered off and washed with ethanol. Acetic acid (10 ml) was added to the filtrate and the solution was refluxed for 1.5 h. The mixture was evaporated to dryness, and the residue was recrystallized from ethanol/water to give 0.18 g (36%) of the title compound. M.p.>220° C. dec.; $^1$H-NMR (DMSO-d$_6$): 7.40-7.70 (m, 3H, ArH), 12.1 (broad s, 1H, NH); IR (KBr): 1700, 1625 cm$^{-1}$; MS (m/e): 246 (68%, M+).

EXAMPLE 24 a. 3-Ethoxalylamino-2-nitrobenzotrifluoride

A solution of ethyl oxalylchloride (0.68 ml 6 mmol) in 10 ml of dry tetrahydrofuran was added dropwise to a solution of 3-amino-2-nitrobenzotrifluoride (0.62 g, 3 mmol) in 30 ml of dry tetrahydrofuran with stirring at 0° C. Then a solution of dry triethylamine (0.84 ml, 6 mmol) in 5 ml of dry tetrahydrofuran was added dropwise. The mixture was stirred at 0° C. for 40 min., and filtered. The filtrate was evaporated to dryness, and the oily residue was triturated with a mixture of ether and light petroleum to give 0.69 g of the diethoxalylamino compound. When heated to reflux in 10 ml of ethanol for 30 min., followed by evaporation to dryness and trituration with ether/light petroleum, the title compound was obtained in a yield of 0.41 g (45%). M.p. 93°-94° C., $^1$H-NMR (CDCl$_3$): 1.43 (t, J=7 Hz, 3H, CH$_3$), 4.50 (q, J=7 Hz, 2H, CH$_2$), 7.58-7.93 (m, 2H, ArH), 8.50-8.80 (m, 1H, ArH), 9.78 (broad s, 1H, NH).

b. 1-Hydroxy-8-trifluoromethylquinoxaline-2,3(1H,4H)-dione

A solution of 3-ethoxalylamino-2-nitrobenzotrifluoride (0.28 g, 0.9 mmol) in 30 ml of 96% ethanol was hydrogenated at atmospheric pressure and room temperature in the presence of 28 mg of 5% platinum on carbon for 5 min. The catalyst was removed by filtration, and the filtrate was evaporated to dryness. The residue was triturated with ether to give 77 mg 34%) of the title compound. M.p. 150° C. dec. $^1$H-NMR (DMSO-d$_6$): 7.20-7.67 (m, 3H, ArH), appr. 12 (very broad s, 1H, NH); IR (KBr): 1700 cm$^{-1}$; MS (m/e): 246 (28%, M+).

EXAMPLE 25 a. 4-Ethoxalylamino-3-nitrobenzotrifluoride

A solution of ethyl oxalylchloride (3.2 ml, 28.2 mmol) in 20 ml of dry tetrahydrofuran was added dropwise to a solution of 4-amino-3-nitrobenzotrifluoride (2.9 g, 14.1 mmol) and dry triethylamine (4.0 ml 28.2 mmol) in 100 ml of dry tetrahydrofuran with stirring at 0° C. Then the mixture was stirred at room temperature for 1 h, and filtered. The filtrate was evaporated to dryness, and the residue was heated to reflux in a small amount of ethanol. After cooling on ice, the precipitate was isolated by filtration and washed with cold ethanol to give 3.9 g (90%) of the title compound. M.p. 124°-125° C.; $^1$H-NMR (DMSO-d$_6$): 1.33 (t, J=7 Hz, 3H, CH$_3$), 4.38 (q, J=7 Hz, CH$_2$), 8.06-8.53 (m, 3H, ArH), 11.5 broad s, 1H, NH).

b. 1-Hydroxy-7-trifluoromethylquinoxaline-2,3(1H,4H)-dione

A solution of 4-ethoxalylamino-S-nitrobenzotrifluoride (0.61 g, 2 mmol) in 40 ml of N,N-dimethylformamide was hydrogenated at atmospheric pressure and room temperature in the presence of 30 mg of 5% platinum on carbon. The catalyst was removed by filtration, and the filtrate was evaporated to dryness. The residue was recrystallized from ethanol/water with decolourizinq carbon to give 0.22 g (45%) of the title compound. M.p.>200° C. dec.; $^1$H-NMR (DMSO-d$_6$): 7.13-7.73

(m, 3H, ArH), 12.4 (broad s, 1H, NH); IR (KBr): 1720, 1660 and 1620 cm$^{-1}$; MS (m/e): 246 (100%, M$^+$).

EXAMPLE 26 a. 4-Bromo-1-ethoxalylamino-2-nitrobenzene

A solution of ethyl oxalylchloride (2.1 ml, 18.7 mmol) in 10 ml of dry tetrahydrofuran was added dropwise to a solution of 1-amino-4-bromo-2-nitrobenzene (4.0 g, 18.4 mmol) and dry triethylamine (2.6 ml, 18.7 mmol) in 100 ml of dry tetrahydrofuran with stirring at 0° C. Stirring was continued for 30 min. at room temperature. Then another equivalent of dry triethylamine and ethyl oxalylchloride was added dropwise to the mixture. The mixture was now refluxed for 15 min, cooled to 0° C. and filtered. The filtrate was evaporated to dryness and the residue was heated to reflux in a small amount of ethanol for 15 min. After cooling on ice, the title compound was obtained by filtration in a yield of 5.65 g (97%). M.p. 168°–169° C.; $^1$H-NMR (DMSO-d$_6$): 1.33 (t, J=7 Hz, 3H, CH$_3$), 4.37 (q, J=7 Hz, 2H, CH$_2$), 8.00–8.37 (m, 3H, ArH), 11.25 (broad s, 1H, NH).

b. 7-Bromo-1-hydroxyquinoxaline-2,3(1H,4H)-dione

A solution of 4-bromo-1-ethoxalylamino-2-nitrobenzene (1.0 g, 3.2 mmol) in 50 ml of N,N-dimethylformamide was hydrogenated at atmospheric pressure and room temperature in the presence of a small amount of Raney-Ni. The catalyst was removed by filtration, and the filtrate was evaporated to dryness. The residue was tritureted with ethanol affording 0.68 g (84%) of the title compound. M.p.>250° C. dec.; $^1$H-NMR (DMSO-d$_6$): 6.98–7.63 (m. 3H ArH) appr. 11.9 (very broad s 1H NH): IR (KBr): 1700 cm$^{-1}$; MS (m/e): 256 (M$^+$, 62%), 258 (M+2)$^+$, 58%).

EXAMPLE 27

5,6-dimethyl-1-hydroxyquinoxaline-2,3(1H,4H)-dione

To a solution of 4.0 g (24.1 mmol) 2,3-dimethyl-6-nitroaniline and 7.0 ml (50.0 mmol) dry triethylamine in 100 ml dry tetrahydrofuran was added a solution of 5.5 ml (49.2 mmol) ethyl oxalylchloride in 20 ml dry tetrahydrofuran. The reaction mixture was stirred at 25° C. for 10 h and then filtered. The filtrate was evaporated in vacuo and the residue in ether was washed with water. The ether-phase was dried and evaporated in vacuo to give an oil.

The oil in 40 ml tetrahydrofuran:dimethylformamide: 25% aqueous ammonia 30:10:1 was hydrogenated at atm. pressure by using 200 mg 5% Pt-c as a catalyst. The reaction mixture was filtered and the filtrate was evaporated in vacuo. The precipitate was dissolved in 20 ml 1N potassium hydroxide and the solution was acidified with concentrated hydrochloric acid. The precipitate was filtered off and washed with water, ethanol and ether to give 0.45 g (9%) of 5,6-dimethyl-1-hydroxyquinoxaline-2,3(1H,4H)-dione. M.p. decomp. $^1$H-NMR (DMSO-d$_6$): 10.8 (1H, broad s), 7.8–7.1 (2H, m), 2.3 (6H, s).

EXAMPLE 28 a. 4-Ethoxalylaminobenzylnitrile

To a solution of 2.6 g (15.4 mmol) 4-aminobenzylnitrile, hydrochloride in 100 ml dry tetrahydrofuran was added 7 ml (50 mmol) dry triethylamine and the reaction mixture was cooled in ice-water. 2.4 ml (21.5 mmol) ethyl oxalylchloride in 20 ml dry tetrahydrofuran was added dropwise and the reaction mixture was stirred at 25° C. for 2 h. The reaction mixture was evaporated in vacuo and the residue was stirred with water. The precipitate was filtered off and washed with ethanol (5 ml) to give 2.3 g (64%) of 4-ethoxalylaminobenzylnitrile. M.p. 99.5°–100.5° C.

b. 4-Ethoxalylamino-3-nitrobenzylnitrile 20 ml 89.1% nitric acid was cooled to 0° C. and 2.0 g (8.6 mmol) 4-ethoxalylbenzylnitrile was added in small portions. After ½ h the reaction mixture was poured into 200 ml ice-water. The crude product was filtered off, washed with water and 5 ml ethanol to give 1.9 g (80%) of 4-ethoxalylamino-3-nitrobenzylnitrile. M.p. 120.5°–121.0° C.

c. 7-Cyanomethyl-1-hydroxyquinoxaline-2,3(1H,4H)-dione

A solution of 1.0 g (3.6 mmol) 4-ethoxalylamino-3-nitrobenzylamine in 30 ml dimethylformamide was hydrogenated at atm. pressure by using 100 mg 5% Pt-c as a catalyst. The reaction mixture was filtered and the filtrate was evaporated in vacuo. The residue was stirred with water and the precipitate was filtered off. The product was washed with water and 5 ml ethanol to give 0.64 g (82%) of 7-cyanomethyl-1-hydroxyquinoxaline-2,3(1H,4H)-dione. M.p. decomp. $^1$H-NMR (DMSO-d$_6$): 12,3 (1H, broad s), 7.6–7.3 (3H, m), 4.2 (2H, s). IR (KBr): 2250 cm$^{-1}$.

d. 7-Carboxymethyl-1-hydroxyquinoxaline-2,3(1H,4H)-dione

A mixture of 0.34 g (1.5 mmol) 7-cyanomethyl-1-hydroxyquinoxaline-2,3(1H,4H)-dione and 10 ml concentrated hydrochloric acid was stirred at 80° C. for 2 h. After cooling to 25° C. the precipitate was filtered off and washed with water to give 0.21 g (58%) of 7-carboxymethyl-1-hydroxyquinoxaline-2,3(1H,4H)-dione. M.p. decomp. MS (m/c): 236 $^1$H-NMR (DMSO-d$_6$) 12.1 (1H, broad s), 7.5–7.1 (3H, m), 3.7 (2H, s).

e. 1-Hydroxy-7-methoxycarbonylmethylquinoxaline-2,3(1H,4H)-dione

A mixture of 0.5 g (2.1 mmol) 7-carboxymethyl-1-hydroxyquinoxaline-2,3(1H,4H)-dione, 5 dr. sulfuric acid (97%) and 50 ml methanol was refluxed for 1 h. After cooling to 25° C. the precipitate was filtered off and washed with ether to give 0.4 g (76%) of 1-hydroxy-7-methoxycarbonylmethyl-quinoxaline-2,3(1H,4H)-dione. M.p. decomp. $^1$H-NMR (DMSO-d$_6$): 12.2 (1H, broad s), 7.5–7.1 (3H, m), 3.9 (2H, s), 3.7 (3H,s).

EXAMPLE 29 a. N-ethoxalyl-4-ethyl-2-nitroaniline

To a solution of 0.9 g (5.4 mmol) 4-ethyl-2-nitroaniline in 50 ml dry tetrahydrofuran was added 1.0 ml (7.1 mmol) dry triethylamine and the reaction mixture was cooled in ice-water. 0.8 ml (7.2 mmol) ethyl oxalylchloride in 10 ml dry tetrahydrofuran was added dropwise and the reaction mixture was stirred at 25° C. for 1 h. The reaction mixture was evaporated in vacuo and the residue was stirred with water. The precipitate was filtered off to give 1.3 g (90%) of N-ethoxalyl-4-ethyl-2-nitroaniline. M.p. 110°–112° C.

b. 7-ethyl-1-hydroxyquinoxaline-2,3(1H,4H)-dione

A solution of 0.25 g (0.9 mmol) N-ethoxalyl-4-butyl-2-nitroaniline in 15 ml tetrahydroduran:dimethylformamide 30:10 was hydrogenated at atm. pressure by using 20 mg 5% Pt-C as a catalyst. The reaction mixture was filtered and 5 dr. 25% aqueous ammonia was added to the filtrate. The filtrate was evaporated in vacuo and the residue was dissolved in 5 ml 1N potassium hydroxide. The solution was filtered and the filtrate was acidified with concentrated hydrochloric acid. The precipitate was filtered off to give 0.06 g (30%) of 7-ethyl-1-1-hydroxyquinoxaline-2,3(1H,4H)-dione. M.p. decomp. $^1$H-NMR (DMSO-d$_6$): 12.0 (1H, broad s), 7.3–7.0 (3H, m), 2.6 (2H, q), 1.2 (3H, t).

EXAMPLE 30 a. 4-chloro-3-trifluoromethylaniline hydrochloride

A solution of 5.0 ml (34 mmol) 2-chloro-5-nitrobenzotrifluoride in 100 ml ethanol was hydrogenated at atm. pressure by using Raney-Ni (1 g) as a catalyst. The reaction mixture was filtered and evaporated in vacuo. The residue was dissolved in ethanol and the solution was acidified with concentrated hydrochloric acid. The precipitate was filtered off to give 6.3 g (81%) of 4-chloro-3-trifluoromethylaniline, hydrochloride. M.p.>200° C.

b. N-Ethoxalyl-4-chloro-3-trifluoromethylaniline

To a solution of 6.0 g (30.7 mmol) 4-chloro-3-trifluoromethylaniline, hydrochloride in 100 ml dry tetrahydrofuran was added 10 ml (71 mmol, cry triethylamine and the reaction mixture was cooled to 0° C. 3 6 ml (xxx mmol) ethyl oxalylchloride in 25 ml dry tetrahydrofuran was added dropwise and the reaction mixture was evaporated in vacuo and the residue was stirred with water. The precipitate was filtered off to give 7.35 g (96%) of N-ethoxalyl-4-chloro-3-trifluoromethylaniline. M.p. 128.5°–129.5° C.

c. N-Ethoxalyl-4-chloro-6-nitro-3-trifluoromethylaniline 6.0 g (20.6 mmol) N-ethoxalyl-4-chloro-3-trifluoromethylaniline was dissolved in 30 ml 100% nitric acid and the reaction mixture was stirred at 25° C. for 16 h. The reaction mixture was poured into 500 ml ice-water. The crude product was filtered off, washed with water and recrystalized (ethanol) to give 4.95 g (72%) of N-ethoxalyl-4-chloro-6-nitro-3-trifluoromethylaniline. M.p. 96.5°–97.5° C.

d. 7-chloro-1-hydroxy-6-trifluoromethylquinoxaline-2,3(1H,4H)- dione

A solution of 2.0 g (5.9 mmol) N-ethoxalyl-4-chloro-6-nitro-3-trifluoromethylaniline in 50 ml dimethylformamide was hydrogenated at atm. pressure by using 200 mg 5% Pt-C as a catalyst. The reaction mixture was stirred with 4N hydrochloric acid and the crude product was filtered off. The crude product was dissolved in 25 ml 1N potassium hydroxide and the solution was acidified with concentrated hydrochloric acid. The precipitate was filtered off to give 310 mg 19%) of 7-chloro-1-hydroxy-6-trifluoromethylquinoxaline-2,3(1H,4H)-dione. M.p. decomp. MS (m/e): 280, $^1$H-NMR (DMSO-d$_6$): 12.2 (1H, broad s), 7.6 (2H, m).

EXAMPLE 31 a. N-ethoxalyl-3,4,5-trichloroaniline

To a solution of 6.0 g (30.5 mmol) 3,4,5-trichloroaniline in 80 ml dry tetrahydrofuran was added 6 ml (42.7 mmol) dry triethylamine. 4 ml (35.8 mmol) ethyl oxalylchloride in 20 ml dry tetrahydrofuran was added dropwise and the reaction mixture was stirred at 25° C. for 1 h. The reaction mixture was evaporated in vacuo and the residue was stirred with water. The precipitate was filtered off to give 5.0 g (55%) of N-ethoxalyl-3,4,5-trichloroaniline. M.p. 148°–151° C.

b. N-ethoxalyl-2-nitro-3,4,5-trichloroaniline 20 ml 100% nitric acid was cooled to 0° C. and 2.0 g (6.8 mmol) N-ethoxalyl-3,4,5-trichloroaniline was added. The reaction mixture was stirred at 0° C. for 10 min. and 200 ml ice-water was added. The precipitate was filtered off, washed with water and ethanol to give 1.2 g (52%) of N-ethoxalyl-2-nitro-3,4,5-trichloroaniline. M.p. 84° C.

c. 1-Hydroxy-6,7,8-trichloroquinoxaline-2,3(1H,4H)-dione

A solution of 2.0 g (5.9 mmol) N-ethoxalyl-2-nitro-3,4,5-trichloroaniline in 50 ml ethanol was hydrogenated at atm. pressure by using 70 mg Pt-C (5%) as a catalyst. The precipitate was filtered off and the filter cake was washed with 10 ml 1N aqueous potassium hydroxide. The filtrate was acidified with concentrated hydrochloric acid and the precipitate was filtered off, washed with water, ethanol and ether to give 0.18 g (11%) of 1-hydroxy-6,7,8-trichloroquinoxaline-2,3(1H,4H)-dione. M.p. decomp. $^1$H-NMR (DMSO-d$_6$): 7.4 (1H, s) MS m/z: 280 (M$^+$, trace, 3Cl), 265 (35%), 237 (100%), 173 (55%).

EXAMPLE 32 a. 4-Amino-3-nitrobenzenesulfonamide

A 100 ml stainless steel autoclave was charged with about 50 ml of liquid ammonia. Then 4-chloro-3-nitrobenzenesulfonamide (5.0 g, 21 mmol) was added and the bomb was heated in an oil bath at 100° C. for 3 h. Excess ammonia was allowed to evaporate, and the solid residue was successively washed with water, cold ethanol and ether to give 3.9 g (85%) of the title compound. M.p. 211.5°–213° C. (ethanol); $^1$H-NMR (DMSO-d$_6$): 6.97 (d,J=9Hz, 1H, H-5), 7.12 (s, 2H, NH$_2$), 7.57 (dd, J$_{6-5}$=9 Hz, J$_{6-2}$2Hz, H-6), 7.70 (broad s, 2H, NH$_2$), 8.22 (d,J 2Hz, H-2).

b. 4-Ethoxalylamino-3-nitrobenzenesulfonamide

A solution of ethyl oxalylchloride (1.7 ml, 15 mmol) in 10 ml of dry tetrahydrofuran was added dropwise to a solution of 4-amino-3-nitrobenzenesulfonamide (3.26 g, 15 mmol) in 100 ml of dry tetrahydrofuran with stirring in an ice bath. A solution of dry triethylamine (2.1 ml, 15 mmol) in 10 ml of dry tetrahydrofuran was added dropwise during 40 min. at 0° C. The mixture was stirred for 1 h at 0° C. and filtered. The filtrate was evaporated to dryness, and the solid residue was washed with cold ethanol and ether to give 4.14 g (87%) of the title compound. M.p. 193°–195° C., $^1$H-NMR (DMSO-d$_6$): 1.32 (t,J=7Hz, 3H, CH$_3$), 4.32 (q,J=7Hz, 2H,CH$_2$), 7.53 (broad s, 2H, SO$_2$NH$_2$), 8.05

(dd,J$_{6-5}$=9Hz, J$_{6-22}$Hz, 1H, H-6), 8.28 (d,J=9Hz, 1H, H-5), 8.42 (d,J 2Hz, 1H,H-2), 11.5 (broad s, 1H, NH).

c. 1-Hydroxy-7-sulfamoylquinoxaline-2,3(1H,4H)-dione

A suspension of 4-ethoxalylamino-3-nitrobenzenesulfonamide (1.59 g, 5 mmol) in 300 ml of 96% ethanol was hydrogenated at atmospheric pressure and room temperature for 30 min. in the presence of 50 mg of 5% platinum on carbon. The catalyst was filtered off and the filtrate was evaporated to dryness. The residue was washed with ethanol and dissolved in 25 ml of saturated aqueous ammonium hydroxide. An undissolved orange residue was removed by filtration, and most of the ammonia was removed from the filtrate under reduced pressure. After treatment with decolourising carbon the filtrate was acidified with conc. hydrochloric acid to give 0.76 g (59%) of the title compound as an off-white precipitate. M.p.>250° C. decomp. (DSC); NMR (DMSO-d$_6$): 7.07–7.93 (m, 3H, ArH), 7.33 (broad s, 2H, NH$_2$), ca. 11.9 (very broad s, 1H, NH or OH), 12.3 (broad s, 1H, OH or NH); IR (KBr): 3300–2100, 1690 cm$^{-1}$; MS (m/e): 257 (10%, M+).

EXAMPLE 33 a.

4-Ethoxalylamino-1-ethoxalylaminosulfonyl-2-trifluoromethylbenzene

Dry triethylamine (54.4 ml, 0.39 mol) was added to a solution of 4-amino-2-trifluoromethylbenzenesulfonamide (31.2 g, 0.13 mol) in 400 ml of dry tetrahydrofuran. Then a solution of ethyl oxalylchloride (43.6 ml, 0.39 mol) in 50 ml of dry tetrahydrofuran was added dropwise at 0° C. The mixture was allowed to stir overnight at room temperature. Triethylamine hydrochloride was filtered off, and the filtrate was evaporated to dryness to give an oil, which was triturated with 150 ml of ethanol. The resulting white precipitate was filtered off and washed with ethanol and ether to yield 46.9 g (82%) of the pure title compound. M.p. 161°–162° C.; $^1$H-NMR (DMSO-d$_6$): 1.25 (t,J=7Hz, 3H, CH$_3$), 1.33 (t,J=7Hz, 3H, CH$_3$), 4.18 (q,J=7Hz, 2H, CH$_2$), 4.30 (q,J=7Hz, 2H, CH$_2$), 8.13–8.41 (m, 3H, ArH), 9.07 (broad s, 1H, NH), 11.43 (broad s, 1H, NH).

b.

1-Ethoxalylamino-4-ethoxalylaminosulfonyl-2-nitro-5-trifluoromethylbenzene

Finely powdered potassium nitrate (11.1 g, 0.11 mol) was added portionwise to a stirred solution of 4-ethoxalyl-amino-1-ethoxalylaminosulfonyl-2-trifluoromethylbenzene (46.2 g, 0.105 mol) in 140 ml of concentrated sulfuric acid while maintaining the temperature below 5° C. Following addition the reaction mixture was allowed to stir at room temperature overnight, poured into 1 l of ice-water and filtered. The crude product was washed with water (1.5 l) and air dried to give the title compound in a yield of 35.5 g (70%). A sample was purified by flash column chromatography with ethyl acetate. M.p. 175°–180° C.; $^1$H-NMR (CDCl$_3$): 1.17–1.67 (m, 6H, 2CH$_3$), 4.07–4.67 (m, 4H, 2CH$_2$), 9.05 (s, 1H, ArH), 9.23 (s, 1H, ArH), 11.73 (broad s, 1H, NH, only one exchangeable proton could be seen).

c.

7-Ethoxalylaminosulfonyl-1-hydroxy-6-trifluoromethylquinoxaline-2,3(1H,4H)-dione A solution of 1-ethoxalylamino-4-ethoxalylaminosulfonyl-2-nitro-5-trifluoromethylbenzene (24.6 g, 50 mmol) in 200 ml of N,N-dimethylformamide was hydrogenated at room temperature and atmospheric pressure in the presence of 1 g of 5% platinum on carbon for 2 h. The catalyst was filtered off and washed with N,N-dimethylformamide. The filtrate was evaporated to dryness and the gummy residue was refluxed with 100 ml of ethanol for about 20 min. The mixture was cooled and the precipitated product was collected by filtration and washed with ethanol and ether to give 12.7 g (59%) of the title compound. M.p. 222° C. decomp. (DSC); IR (KBr): 1685 cm$^{-1}$; $^1$H-NMR (DMSO-d$_6$): 1.25 (t,J=7Hz, 3H, CH$_3$), 4.23 (q,J=7Hz, 2H, CH$_2$), 7.67 (s, 1H, ArH), 8.30 (s, 1H, ArH), 10.8 (broad s, 2H, exchangeable), 12.5 (broad s, 1H, exchangeable).

d.

1-Hydroxy-7-sulfamoyl-6-trifluoromethylquinoxaline-2,3(1H,4H)-dione

A suspension of 7-ethoxalylaminosulfonyl-1-hydroxy-6-trifluoromethylquinoxaline-2,3(1H,4H)-dione (12.0 g, 28 mmol) in 150 ml of 1M hydrochloric acid was heated at reflux for 2 h with stirring. The cooled mixture was filtered and the isolated solid was washed with water and light petroleum. The crude product was recrystallized from water with decolourizing charcoal and dried in vacuo over phosphorous pentoxide for 3 h to give 7.1 g (77%) of the pure title compound. M.p. 296° C. decomp. (DSC); IR (KBr): 1700, 1615 cm$^{-1}$; $^1$H-NMR (DMSO-d$_6$): 7.67 (s, 1H, ArH), 7.77 (s, 2H, NH$_2$), 8.26 (s, 1H, ArH), 12.2 (broad s, 2H, NH and OH); MS m/e: 325 (M+, 100%).

EXAMPLE 34 a. 2-Bromo-4-methoxy-5-nitroacetophenone

A solution of 2-bromo-4-methoxyacetophenone (4.58 g, 20 mmol) in 50 ml of acetic anhydride was cooled to −15° C. and a few drops of conc. sulfuric acid was added. A solution of 100% nitric acid (0.83 ml, 20 mmol) in 5 ml of acetic anhydride was added dropwise, while the temperature was maintained at −10° to −15° C. After 1 h of additional stirring at this temperature, the mixture was poured onto 200 ml of ice-water. The separated white solid was collected by filtration and washed with water, ethanol and ether to give 4.4 g (80%) of a mixture of 2-bromo-4-methoxy-5-nitroacetophenone and 2-bromo-4-methoxy-3-nitroacetophenone. Recrystallization from 96% ethanol afforded 2.83 g (52%) of the 5-nitro isomer. M.p. 116°–117 C; $^1$H-NMR (CDCl$_3$): 2.65 (s, 3H, COCH$_3$), 4.00 (s, 3H, OCH$_3$), 7.30 (s, 1H, ArH), 8.10 (s, 1H, ArH).

The mother liquor was evaporated to dryness and subjected to column chromatography with ether. The 5-nitro isomer was eluted first (0.50 g (9%)) followed by the 3-nitro isomer in a yield of 0.68 g (12%); m.p. 119°–120° C.

b. 2-Acetyl-5-methoxy-4-nitrobenzonitrile

A solution of 2-bromo-4-methoxy-5-nitroacetephenone (2.1 g, 7.5 mmol) in 8 ml of dry N,N-dimethylformamide was heated to 80° C. with stirring and cuprous cyanide (1.34 g, 15 mmol) was added. The reaction mixture was stirred for 1 h at 80° C. and was then allowed to cool to room temperature. A solution of ferric chloride hexahydrate (4.0 g of FeCl$_3$.6H$_2$O in 1 ml of 12M hydrochloric acid and 6 ml of water) was added, and the mixture was stirred at 60° C. for 30 min. Then the mixture was poured into 100 ml of water, and the separated solid was isolated by filtration. Recrystallization from ethanol with decolourising charcoal afforded 1.31 g (79%) of the title compound. M.p. 224°–226° C.; IR (KBr): 2232 cm$^{-1}$ (CN); $^1$H-NMR (DMSO-d$_6$): 2.60 (s, 3H, COCH$_3$), 4.03 (s, 3H, OCH$_3$), 7.95 (s, 1H, ArH), 8.57 (s, 1H, ArH).

c. 4-Acetyl-5-cyano-2-nitroaniline

Ammonia was bubbled through a solution of 2-acetyl-5-methoxy-4-nitrobenzonitrile (0.80 g. 3.6 mmol) in 10 ml of dry dimethylsulfoxide with stirring at 80° C. for 45 min. Then the solution was poured into 100 ml of ice-water The product was isolated by filtration and washed with water to afford 0.71 g (95%) of the title compound. M.p. 255°–260° C.; $^1$H-NMR (DMSO-d$_6$): 2.57 (s, 3H, COCH$_3$), 7.50 (s, 1H, ArH), 8.20 (broad s, 2H, NH2), 8.65 (s, 1H, ArH).

d. 1-Acetyl-2-cyano-4-ethoxalylamino-5-nitrobenzene

Dry triethylamine (1.7 ml. 12 mmol) was added to a solution of 4-acetyl-5-cyano-2-nitroaniline (0.62 g, 3 mmol) in 100 ml of dry tetrahydrofuran. Then a solution of ethyl oxalylchloride (1.34 ml, 12 mmol) was added dropwise with stirring at room temperature. After 1 h the mixture was refluxed for 2 h and allowed to cool to room temperature. The suspension was filtered and the filtrate was evaporated to dryness to give an oil, which was induced to solidify by treatment with a small amount of ethanol. Yield 0.50 g (55%). M.p. 142°–144° C.; $^1$H-NMR (CDCl$_3$): 1.47 (t,J=7Hz, 3H, CH$_3$), 2.75 (s, 3H, COCH$_3$), 4.47 (q,J=7Hz, 2H, CH$_2$), 8.80 (s, 1H, ArH), 9.27 (s, 1H, ArH), 11.94 (broad s, 1H, NH).

e. 7-Acetyl-6-cyano-1-hydroxyquinoxaline-2,3(1H,4H)-dione

A solution of 1-acetyl-2-cyano-4-ethoxalylamino-5-nitrobenzene (0.31 g, 1 mmol) in 10 ml of N,N-dimethylformamide was hydrogenated at atmospheric pressure and room temperature for 1 h in the presence of 30 mg of 5% platinum on carbon. The catalyst was filtered off, and the filtrate was evaporated to dryness. The pure product was obtained after recrystallization from water with decolourising charcoal. Yield 0.12 g (49%). M.p. 340.8° C. decomp. (DSC); IR (KBr): 2238 (CN), 1692 cm$^{-1}$; $^1$H-NMR (DMSO-d$_6$): 2.62 (s, 3H, CH$_3$), 7.43 (s, 1H, ArH), 7.96 (s, 1H, ArH), ca. 12 (very broad s, 2H, NH and OH); MS m/e: 245 (M$^+$, 26%).

EXAMPLE 35

1-Benzyloxy-7-cyano-6-trifluoromethylquinoxaline-2,3(1H,4H)-dione

To a solution of 0.4 g (1.5 mmol) 7-cyano-1-hydroxy-6-trifluoromethylquinoxaline-2,3(1H 4H)-dione in 30 ml ethanol was added 10 ml 0.5M phosphate buffer pH 7.4. The mixture was added 0.4 ml (2.3 mmol) benzylbromide, and then stirred at 25° C. for 4 h. The precipitated product was filtered off and washed with water and ethanol to give 0.48 g (91%) 1-benzyloxy-7-cyano-6-trifluoromethylquinoxaline-2,3(1H,4H)-dione. M.p. 265° C. (ethyl acetate - light petroleum). NMR (DMSO-d$_6$): 8.0–7.3 (7H, m), 5.25 (2H, s).

EXAMPLE 36

1-Allyloxy-7-cyano-6-trifluoromethylquinoxaline-2,3(1H,4H)-dione

To a solution of 0.4 g (1.5 mmol) 7-cyano-1-hydroxy-6-trifluoromethylquinoxaline-2,3(1H,4H)-dione in 40 ml ethanol was added 20 ml 0.5 M phosphate buffer pH 7.4. The mixture was added 0.8 ml (9.3 mmol) allyl bromide, and then stirred at 25° C. for 4 h. Addition of 80 ml water gave 0.33 g (72%) 1-allyloxy-7-cyano-6-trifluoromethylquinoxaline-2,3(1H,4H)-dione as a precipitate. M.p. 239° C. decomp. (methanol-water). NMR (DMSO-d$_6$) 7.9 (1H, s), 7.6 (1H, s), 6.1 (1H, m), 5.4 (2H, m), 4.7 (2H, d).

EXAMPLE 37

7-Cyano-1-methoxy-6-trifluoromethylquinoxaline-2,3(1H,4H)-dione

To a solution of 0.3 g (1.1- mmol) 7-cyano-1-hydroxy-6-trifluoromethylquinoxaline 2,3(1H,4H)-dione in 30 ml ethanol was added 15 ml 0.5M phosphate buffer pH 7.4. The mixture was added 1 ml (16 mmol) iodomethane, and then stirred overnight. The reaction mixture was evaporated, and the residue was stirred with water to give a precipitate. Recrystallization (dimethylformamide-water) gave 0.2 g (63%) of 7-cyano-1-methoxy-6-trifluoromethylquinoxaline-2,3(1H,4H)-dione. M.p. 250° C. decomp. $^1$H-NMR (DMSO-d$_6$): 7.9 (1H, s), 7.6 (1H, s), 4.07 (3H, s).

EXAMPLE 38

7-Cyano-1-cyclohexyloxy-6-trifluoromethyl-quinoxaline-2,3(1H,4H)-dione

To a solution of 0.3 g (1.1 mmol) 7-cyano-1-hydroxy-6-trifluoromethylquinoxaline -2,3(1H,4H)-dione in 30 ml ethanol was added 0.7 ml triethylamine and 1.5 ml (12 mmol) cyclohexylbromide. The reaction mixture was refluxed for 7 days and then evaporated in vacuo. The residue was stirred with water to give a precipitate (0.25 g. Recrystallization (dimethylformamide-water) gave 0.17 g (44%) of 7-cyano-1-cyclohexyloxy-6-trifluoromethylquinoxaline-2,3(1H,4H)-dione). M.p. 259° C. decomp. $^1$H-NMR (DMSO-d$_6$): 8.0 (1H, s), 7.6 (1H, s), 4.3 (1H, m), 1.4 (8H, m).

EXAMPLE 39

1-Carboxymethyloxy-7-cyano-6-trifluoromethyl-quinoxaline-2,3(1H,4H)-dione

To a solution of 0.3 g (1.1 mmol) 7-cyano-1-hydroxy-6-trifluoromethylquinoxaline-2,3(1H,4H)-dione in 30 ml ethanol was added 30 ml 0.5M phosphate buffer pH 7.4. The mixture was added 0.9 g (6.5 mmol) bromoacetic acid and then stirred at 25° C. for 10 days. 4N hydrochloric acid was added to pH 1, and then the reaction mixture was evaporated in vacuo. The residue was stirred with water to give 0.27 g (74%) of 1-carboxymethyloxy-7-cyano-6-trifluoromethylquinoxaline-2,3(1H,4H)-dione. M.p. 257° C. 1H-NMR (DMSO-d$_6$): 8.2 (1H, s), 7.6 (1H, s), 4.8 (2H, s).

EXAMPLE 40 a. 5-Amino-2-chlorobenzonitril

A solution of 10.0 g (54.8 mmol) 2-chloro-5-nitrobenzonitril in 500 ml ethanol was hydrogenated at 40 psi by using 0.5 g 5% Pd-C as a catalyst. The catalyst was filtered off and the filtrate was evaporated in vacuo. Recrystallization (ethanol-water) gave 3.6 g (43%) 5-amino-2-chlorobenzonitril. M.p. 129–130° C.

b. 2-Chloro-5-ethoxalylaminobenzonitril

To a solution of 3.5 q (23.4 mmol) 5-amino-2-chlorobenzonitril and 3.6 ml (26.2 mmol) dry triethylamine in 200 ml dry tetrahydrofuran was added a solution of 3.0 ml (26.9 mmol) ethyl oxalylchloride in 20 ml of dry tetrahydrofuran. Stirring was continued at 25° C. for 2 h, and then the reaction mixture was filtered. The filtrate was evaporated in vacuo. The residue was stirred with water to give 5.8 g (99%)2-chloro-5-ethoxalylaminobenzonitril. M.p. 182°–183° C.

c. 2-Chloro-5-ethoxalylamino-4-nitrobenzonitril

To 50 ml ice-cooled 100% nitric acid was added gradually 5.0 g (19.8 mmol) 2-chloro-5-ethoxalylaminobenzonitril. Stirring was continued at 0° C. for 90 min. The reaction mixture was poured into 300 ml ice-water to give 5.2 g of the 6-nitro isomer. The water phase was extracted with ethyl acetate to give 0.7 g as an oil. The crude product was purified by column chromatography to give 0.6 g (10%) 2-chloro-5-ethoxalylamino-4-nitrobenzonitril. M.p. 80°–82° C. $^1$H-NMR (CDCl$_3$): 8.6 (1H, s), 8.3 (1H, s), 4.4 (2H, q), 1.4 (3H, t).

d. 7-Chloro-6-cyano-1-hydroxyquinoxaline-2,3(1H,4H)-dione

To a solution of 0.6 g (2.0 mmol) 2-chloro-5-ethoxalylamino-4-nitrobenzonitril in 50 ml tetrahydrofuran was added 15 ml dimethylformamide and 0.7 ml 25% aqueous ammonia. The mixture was hydrogenated at atm. pressure by using 0.1 g Pd-C as a catalyst. The catalyst was filtered off, and the filter cake was washed with tetrahydrofuran. The precipitated product was dissolved in 1N aqueous potassium hydroxide. Addition of concentrated hydrochloric acid to pH 1 gave 0.25 g (50%) 7-chloro-6-cyano-1-hydroxyquinoxaline-2,3(1H,4H)-dione. M.p. 320° C. decomp. $^1$H-NMR (DMSO-d$_6$): 7.6 (1H, s), 7.5 (1H, s).

EXAMPLE 41 a. 3-Ethoxalylaminobenzonitril

To a solution of 2.5 g (21.1 mmol) 3-aminobenzonitril and 3.0 ml (21.8 mmol) dry triethylamine in 150 ml dry tetrahydrofuran. The reaction mixture was stirred at 25° C. for 2 h and then filtered. The filtrate was evaporated in vacuo and the residue was stirred with water to give 4.35 g (95%) 3-ethoxalylaminobenzonitril. M.p. 149°–150° C.

b. 3-Ethoxalylamino-4-nitrobenzonitril 50 ml 100% nitric acid was cooled to ca. −5° C. and then gradually added 5 g (22.9 mmol) 3-ethoxalylaminobenzonitril. Stirring was continued at 0° C. for 1 h. The reaction mixture was poured into 200 ml ice-water to give a precipitate (4.1 g) containing a mixture of the 2- and 6-nitro isomers. The water phase was extracted with ethyl acetate to give an oil (1.0 g). The crude product was submit ted to column chromatography to give 0.65 g (11%) of 3-ethoxalylamino-4-nitrobenzonitril as an oil. $^1$H-NMR (CDCl$_3$) 9.2 (1H, d, J=2Hz), 8.4 (1H, d, J=8Hz), 7.6 (1H, dd, J=2Hz and 8Hz), 4.5 (2H, q), 1.5 (3H, t).

c. 6-Cyano-1-hydroxyquinoxaline-2,3(1H,4H)-dione

A solution of 0.5 g (1.9 mmol) 3-ethoxalylamino-4-nitrobenzonitril in 50 ml ethanol was hydrogenated at atm. pressure by using 25 mg 5% Pt-C as a catalyst. The catalyst was filtered off, and the filtrate was evaporated in vacuo. Cyclization was achieved by evaporation with acetic acid. Recrystallization (dimethylformamide-water) gave 0.25 g (65%) of 6-cyano-1-hydroxyquinoxaline-2,3(1H,4H)-dione. M.p. 250° C. decomp. $^1$H-NMR (DMSO-d$_6$) 7.53 (s) and 7.40 (s)—a total of 3H.

In conclusion, from the foregoing, it is apparent that the present invention provides novel neurologically-effective quisqualate antagonist quinoxaline compounds and salts thereof, having advantageous and unpredictable properties as well as novel pharmaceutical compositions thereof and method of treating therewith, all possessed of the foregoing more specifically-enumerated characteristics and advantages.

It is to be understood that the invention is not to be limited to the exact details of operation, or to the exact compositions, methods, procedures, or embodiments shown and described as obvious modifications and equivalents will be apparent to one skilled in the art, and the invention is therefore to be limited only by the full scope of the appended claims.

We claim:

1. A quinoxaline compound having the formula I

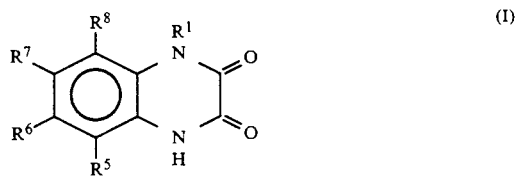

wherein
R$^1$ is hydroxy, methoxy, propenyloxy, cyclohexyloxy, carboxymethyloxy, benzyloxy or OCOR$^2$, wherein R$^2$ is C$_{1-2}$-alkyl, ethoxy, phenoxy or phenyl;
R$^5$ is hydrogen, hydroxy, methyl, NO$_2$, halogen, CN, CF$_3$, C$_{1-4}$-alkoxy, SO$_2$NR'R' or SO$_2$R', wherein R' is hydrogen or C$_{1-4}$-alkyl;
R$^6$ is hydrogen, hydroxy, methyl, NO$_2$, halogen, CN, CF$_3$, C$_{1-4}$-alkoxy, SO$_2$NR'R' or SO$_2$R', wherein R' is hydrogen or C$_{1-4}$-alkyl;
R$^7$ is hydrogen, hydroxy, C$_{1-2}$-alkyl, NO$_2$, halogen, CN, CF$_3$, C$_{1-4}$-alkoxy, acetyl, cyanomethyl, carboxymethyl, methoxycarbonylmethyl, SO$_2$NHCOCOOC$_2$H$_5$, SO$_2$NR'R' or SO$_2$R', wherein R' is hydrogen or C$_{1-4}$-alkyl;
R$^8$ is hydrogen, hydroxy, NO$_2$, halogen, CN, CF$_3$, C$_{1-4}$-alkoxy, SO$_2$NR'R' or SO$_2$R', wherein R' is hydrogen or C$_{1-4}$-alkyl;
provided that R$^1$ is not hydroxy, when
i) R$^5$ is methyl, R$^6$ is hydrogen, R$^7$ is hydrogen and R$^8$ is hydrogen; or
ii) R$^5$ is hydrogen, R$^6$ is CF$_3$, R$^7$ is hydrogen and R$^8$ is hydrogen.

2. The compound 7-cyano-1-hydroxy-6-trifluoromethylquinoxaline-2,3(1H,4H)-dione.

3. The compound 7-chloro-1-hydroxy-6-trifluoromethylquinoxaline-2,3(1H,4H)-dione.

4. The compound 1-hydroxy-7-sulfamoyl-6-trifluoromethylquinoxaline-2,3(1H,4H)-dione.

5. The compound 7-acetyl-6-cyano-1-hydroxyquinoxaline-2,3(1H,4H)-dione.

6. A pharmaceutical composition useful as a neuroleptic comprising an effective amount of a compound having the formula I or a pharmaceutically acceptable salt thereof together with a pharmaceutically acceptable carrier or diluent, wherein formula I is as follows:

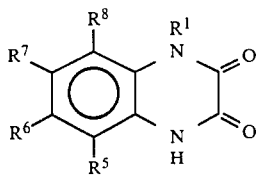 (I)

wherein
- $R^1$ is hydroxy, methoxy, propenyloxy, cyclohexyloxy, carboxymethyloxy, benzyloxy or $OCOR^2$, wherein $R^2$ is $C_{1-2}$-alkyl, ethoxy, phenoxy or phenyl;
- $R^5$ is hydrogen, hydroxy, methyl, $NO_2$, halogen, CN, $CF_3$, $C_{1-4}$-alkoxy, $SO_2NR'R'$ or $SO_2R'$, wherein $R'$ is hydrogen or $C_{1-4}$-alkyl;
- $R^6$ is hydrogen, hydroxy, methyl, $NO_2$, halogen, CN, $CF_3$, $C_{1-4}$-alkoxy, $SO_2NR'R'$ or $SO_2R'$, wherein $R'$ is hydrogen or $C_{1-4}$-alkyl;
- $R^7$ is hydrogen, hydroxy, $C_{1-2}$-alkyl, $NO_2$, halogen, CN, $CF_3$, $C_{1-4}$-alkoxy, acetyl, cyanomethyl, carboxymethyl, methoxycarbonylmethyl, $SO_2NHCOCOOC_2H_5$, $SO_2NR'R'$ or $SO_2R'$, wherein $R'$ is hydrogen or $C_{1-4}$-alkyl;
- $R^8$ is hydrogen, hydroxy, $NO_2$, halogen, CN, $CF_3$, $C_{1-4}$-alkoxy, $SO_2NR'R'$ or $SO_2R'$, wherein $R'$ is hydrogen or $C_{1-4}$-alkyl;

provided that $R^1$ is not hydroxy, when
  i) $R^5$ is methyl, $R^6$ is hydrogen, $R^7$ is hydrogen and $R^8$ is hydrogen; or
  ii) $R^5$ is hydrogen, $R^6$ is $CF_3$, $R^7$ is hydrogen and $R^8$ is hydrogen.

7. A pharmaceutical composition according to claim 6 in the form of an oral dosage unit containing about 50–200 mg of the active compound.

8. A method of treating an indication related to hyperactivity of the excitatory neurotransmitters, in a subject in need thereof, which comprises the step of administering to the said subject an effective amount of a compound having the formula I or a pharmaceutically acceptable salt thereof together with a pharmaceutically acceptable carrier or diluent, wherein formula I is as follows:

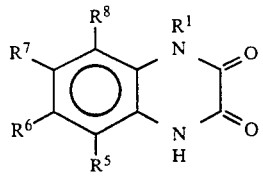 (I)

wherein
- $R^1$ is hydroxy, methoxy, propenyloxy, cyclohexyloxy, carboxymethyloxy, benzyloxy or $OCOR^2$, wherein $R^2$ is $C_{1-2}$-alkyl, ethoxy, phenoxy or phenyl;
- $R^5$ is hydrogen, hydroxy, methyl, $NO_2$, halogen, CN, $CF_3$, $C_{1-4}$-alkoxy, $SO_2NR'R'$ or $SO_2R'$, wherein $R'$ is hydrogen or $C_{1-4}$-alkyl;
- $R^6$ is hydrogen, hydroxy, methyl, $NO_2$, halogen, CN, $CF_3$, $C_{1-4}$-alkoxy, $SO_2NR'R'$ or $SO_2R'$, wherein $R'$ is hydrogen or $C_{1-4}$-alkyl;
- $R^7$ is hydrogen, hydroxy, $C_{1-2}$-alkyl, $NO_2$, halogen, CN, $CF_3$, $C_{1-4}$-alkoxy, acetyl, cyanomethyl, carboxymethyl, methoxycarbonylmethyl, $SO_2NHCOCOOC_2H_5$, $SO_2NR'R'$ or $SO_2R'$, wherein $R'$ is hydrogen or $C_{1-4}$-alkyl;
- $R^8$ is hydrogen, hydroxy, $NO_2$, halogen, CN, $CF_3$, $C_{1-4}$-alkoxy, $SO_2NR'R'$ or $SO_2R'$, wherein $R'$ is hydrogen or $C_{1-4}$-alkyl;

provided that $R^1$ is not hydroxy, when
  i) $R^5$ is methyl, $R^6$ is hydrogen, $R^7$ is hydrogen and $R^8$ is hydrogen; or
  ii) $R^5$ is hydrogen, $R^6$ is $CF_3$, $R^7$ is hydrogen and $R^8$ is hydrogen.

9. A method according to claim 8 wherein said compound is administered in the form of an oral dosage unit containing about 50–200 mg of the active compound.

10. A method according to claim 8 wherein said compound is administered in the form of a pharmaceutical composition together with a pharmaceutically acceptable carrier or diluent.

* * * * *